US008614246B2

(12) United States Patent
Schmidt et al.

(10) Patent No.: US 8,614,246 B2
(45) Date of Patent: Dec. 24, 2013

(54) INDOLE DERIVATIVES FOR TREATING NEURODEGENERATIVE DISEASES

(75) Inventors: Fanny Schmidt, Chatenay Malabry (FR); Bruno Figadere, Saint Cheron (FR); Rita Raisman-Vozari, Paris (FR); Pierre Champy, Palaiseau (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 66 days.

(21) Appl. No.: 13/254,370

(22) PCT Filed: Mar. 2, 2010

(86) PCT No.: PCT/EP2010/052596
§ 371 (c)(1),
(2), (4) Date: Sep. 1, 2011

(87) PCT Pub. No.: WO2010/100133
PCT Pub. Date: Sep. 10, 2010

(65) Prior Publication Data
US 2011/0319387 A1    Dec. 29, 2011

(30) Foreign Application Priority Data

Mar. 2, 2009    (FR) ..................................... 09 51303

(51) Int. Cl.
*A61K 31/4045*    (2006.01)
*C07D 209/14*    (2006.01)

(52) U.S. Cl.
USPC ......................................... 514/415; 548/504

(58) Field of Classification Search
USPC ......................................... 548/504; 514/415
See application file for complete search history.

(56) References Cited

FOREIGN PATENT DOCUMENTS

EP    1 020 179 A2    7/2000

OTHER PUBLICATIONS

Fowler, et al. Document No. 139:375206, retrieved from CAPLUS, Jul. 10, 2003.*
Wiart, et al. Document No. 136:51066, retrieved from CAPLUS, Sep. 26, 2001.*
Sciortino, et al. Document No. 70:37347, retrieved from CAPLUS, May 12, 1984.*
Urban. Document No. 53:63247, retrieved from CAPLUS, Apr. 22, 2001.*
Munch, et al. Document No. 131:115556, retrieved from CAPLUS, Jun. 22, 1999.*
Greff. Document No. 128:192929, retrieved from CAPLUS, Mar. 2, 1998.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/O9/24/alzheimers.drug.ap/indexhtml>.*
Brimblecombe, "Hyperthermic Effects of Some Tryptamine Derivatives in Relation to Their Behavioural Activity", Int. J. Neuropharmacol., 1967, 6(5), pp. 423-429.
Chavez et al., "Tryptamine Derived Amides and Acetogenins from the Seeds of Rollinia Mucosa", J. Nat. Prod., 1999, 62 (8), pp. 1119-1122.
Coowar et al., J. Med. Chem., 2004, 47(25), pp. 6270-6282.
D'Amato et al., "Aminergic Systems in Alzheimer's Disease and Parkinson's Disease", Ann. Neurol. 1987, 22(2), pp. 229-236, XP-002533320.
Glennon et al., "Binding of O-Alkyl Derivatives of Serotonin at Human 5-HT1DB Receptors", J. Med. Chem. 1996, 39, pp. 314-322, XP 002035629.
Guerreiro et al., "Paraxanthine, the Primary Metabolite of Caffeine, Provides Protection Against Dopaminergic Cell Death Via Stimulation of Ryanodine Receptor Channels", Molecular Pharmacology 2008, 74(4), pp. 980-989.
Kalir et al., "Synthesis and Pharmacological Activity of Alkylated Tryptamines", J. of Med. Chem. 1966, 9(3), pp. 341-344, XP-002533319.
Leonard et al., "The Effects of Some Tryptamine Derivatives on Brain Monoamines and Their Precursor Amino Acids", Neuropharmacology, 1972, 11(3), pp. 373-384.
Mourlevat et al., "Prevention of Dopaminergic Neuronal Death by Cyclic AMP in Mixed Neuronal/Glial Mesencephalic Cultures Requires the Repression of Presumptive Astrocytes", Molecular Pharmaology, 2003, 64(3), pp. 578-586.
Nicholson et al., "5-hydroxytryptamine (5-HT, serotonin) and Parkinson's disease-opportunities for novel therapeutics to reduce the problems of levodopa therapy", European Journal of Neurology 2002, 9(3), pp. 1-6.
Offermeier et al., "Serotonin. II. Structural variation and action", Arch. Int. Pharmacodyn. 1966, 164(1), pp. 216-245, XP-009118556.
Suckling et al., Non-Selective inhibition of GABA and 5-HT uptake systems in rat brain IV N-n-alkyl hydroxybenzylamine and N-n-alkyl phenylethylamine derivatives, Biochemical Pharmacology, vol. 34, No. 23, pp. 4173-4177, 1985.
Wu et al., "Tryptamine-Derived Amides and Alkaloids from the Seeds of Annona Atemoya", J. Nat. Prod., 2005, 68 (3), pp. 406-408.

* cited by examiner

*Primary Examiner* — Shawquia Young
(74) *Attorney, Agent, or Firm* — Birch, Stewart, Kolasch & Birch, LLP

(57) ABSTRACT

The invention relates to a compound of the following formula (I),

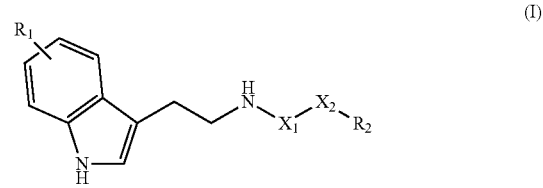

(I)

or to a pharmaceutically acceptable salt thereof or to a stereoisomer or mixture of stereoisomers at any proportions, where: $X_1$ is a $CH_2$ or C=O group; $X_2$ is a linear saturated or unsaturated carbohydrate chain with 8 to 24 carbon atoms; $R_1$ is a hydrogen atom or an OH or ($C_1$-$C_6$)alkoxy group such as methoxy; and $R_2$ is a $CH_3$ or $CH_2$ $OR_3$ group, with $R_3$ being a hydrogen atom or a ($C_1$-$C_6$)alkyl, CO—($C_1$-$C_6$)alkyl or NH—($C_1$-$C_6$)alkyl group. The invention also relates to the use of said compound as a drug, in particular for treating neurodegenerative diseases, and to a method for preparing same.

24 Claims, 4 Drawing Sheets

INDOLE DERIVATIVES FOR TREATING NEURODEGENERATIVE DISEASES

This invention relates to compounds with an indole pattern substituted by an aliphatic chain useful for the treatment of neurodegenerative diseases, and the method for their preparation and their use.

With the increase in life expectancy, there are more and more persons suffering from neurodegenerative diseases such as Alzheimer's disease and Parkinson's disease.

A neurodegenerative disease is characterised by a progressive apoptotic death of particular neuron sub-populations related to a functional deficit of affected transmission axes. This type of disease progressively affects functioning of the central nervous system and particularly the brain, the disease possibly developing more or less quickly (a few weeks to a few years) and often irreversibly. Several functions such as motricity, language, memory, perception and cognition can be affected, depending on the region of the central nervous system affected by the disease. The most frequent neurodegenerative diseases are Alzheimer's disease and Parkinson's disease.

Alzheimer's disease that affects about 24 million persons throughout the world is a disease of the brain tissue that causes progressive and irreversible loss of mental functions. The first symptom is loss of the memory of recent events (amnesia), followed by cognitive deficits affecting language (aphasia), organisation of movements (apraxia), visual recognition (agnosia) and executive functions (such as decision making and planning).

Parkinson's disease affects the central nervous system and causes progressive disorders in motor functions, particularly trembling of the body.

The therapeutic use of neurotrophines described in maintenance of various neuron populations has been proposed for remedial purposes. Although the administration of recombining neurotrophines in injured animal models has demonstrated a beneficial effect on neuron survival, their use in man was quickly limited, even though it was at first encouraging. The very strong hydrophilic nature of these compounds that prevents their passage through the blood-brain barrier and their fast enzymatic degradation, make repeated intra-cranial administration necessary and this generates dramatic side effects.

Furthermore, other medicines prescribed for these different neurodegenerative diseases can only reduce the rate of progress of the disease, none of them is capable of curing the disease or even stopping its progress.

Therefore there is a real need at the present time to find new more active molecules capable of passing through the blood-brain barrier for the treatment of these neurodegenerative diseases.

The indole nucleus is a pattern present in many natural or non-natural compounds with various biological activities since anti-microbial, anti-parasite, anti-oxidant, neurotrophic and anti-inflammatory activities have been reported.

Compounds with a long aliphatic chain grafted onto an indole have been reported for their neurotrophic properties (Coowar D. et al. *J. Med. Chem.* 2004, 47, 6270). These structures have already been described and have a chain directly coupled to the indolic cycle, however no structure derived from tryptamine has been studied for these properties.

Interestingly, the inventors then discovered that natural derivatives of tryptamine of the long chain N-acyltryptamine type extracted from some plants in the Annonaceae family, and particularly *Annona atemoya, Annona reticulata* and *Rollinia mucosa* (Wu Y.-C. et al. *J. Nat. Prod.* 2005, 68(3), 406-408) and other synthetic analogues derived from tryptamine, had a protective and differentiating activity towards dopaminergic neurons in culture.

Therefore the purpose of this invention is a compound of the following formula (I):

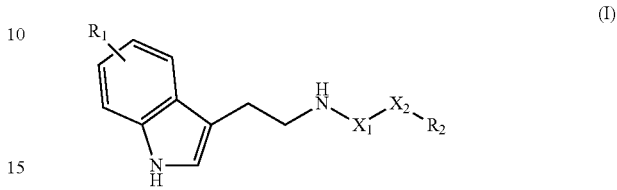

or a pharmaceutically acceptable salt of this compound, a stereoisomer or a mixture of stereoisomers in any proportion, and particularly a mixture of enantiomers, and particularly a racemate, in which:
$X_1$ represents a $CH_2$ or $C=O$ group;
$X_2$ represents a saturated or unsaturated linear hydrocarbon chain comprising 1 to 24, and preferably 8 to 22, carbon atoms;
$R_1$ represents a hydrogen atom or an OH or $(C_1-C_6)$alcoxy group such as methoxy; and
$R_2$ represents a $CH_3$ or $CH_2OR_3$ group, where $R_3$ represents an atom of hydrogen or a $(C_1-C_6)$alkyl, CO—$(C_1-C_6)$alkyl or NH—$(C_1-C_6)$alkyl group;

for use as a medicine, particularly as a neurotrophic or neuroprotective medicine, advantageously intended for the treatment or prevention of neurodegenerative diseases such as Alzheimer's disease, Parkinson's disease, multiple sclerosis or cerebrovascular accidents.

For the purpose of this invention, a "$(C_1-C_6)$alkyl" group refers to a saturated, linear or ramified hydrocarbon chain comprising 1 to 6 carbon atoms, and particularly methyl, ethyl, n-propyl, isopropyl, n-butyl, iso-butyl, sec-butyl, tert-butyl, n-pentyl, n-hexyl groups. Preferably, it is a methyl group.

For the purposes of this invention, a "$(C_1-C_6)$alcoxy" group refers to a $(C_1-C_6)$ alkyl group as defined above bound to the molecule through an oxygen atom. In particular it refers to methoxy, ethoxy, n-propoxy, isopropoxy, n-butoxy, iso-butoxy, sec-butoxy, tert-butoxy, n-pentoxy groups. It is preferably a methoxy group.

For the purposes of this invention, a "CO—$(C_1-C_6)$alkyl" group refers to a $(C_1-C_6)$ alkyl group as defined above bound to the module through a CO group. In particular, it may be an acyl group (—$COCH_3$), or an ethylcarbonyl group (—$COCH_2CH_3$).

For the purposes of this invention, an "NH—$(C_1-C_6)$alkyl" group refers to a $(C_1-C_6)$ alkyl group as defined above bound to the module through an NH group.

For the purposes of this invention, "unsaturated" means that the hydrocarbon chain may comprise one or several unsaturation(s).

For the purposes of this invention, "unsaturation" means a double or triple bond and preferably a double bond.

For the purposes of this invention, "pharmaceutically acceptable" refers to what is useful in preparation of a pharmaceutical composition and that is generally safe, not toxic and neither biologically nor otherwise undesirable and that is acceptable for veterinary use and for human pharmaceutical use.

For the purposes of this invention, "pharmaceutically acceptable salts" of a compound refer to salts that are pharmaceutically acceptable as defined herein and that have the required pharmacological activity of the parent compound. Such salts include:

(1) hydrates and solvates (2) acid additive salts formed from inorganic acids such as hydrochloric acid, hydrobromic acid, sulphuric acid, nitric acid, phosphoric and the like; or formed from organic acids such as acetic acid, benzenesulfonic acid, benzoic acid, camphresulfonic acid, citric acid, ethane-sulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic and the like; and (3) the salts formed when an acid proton present in the parent compound is replaced by a metallic ion, for example an alkaline metal ion (for example $Na^+$, $K^+$ or $Li^+$), an alkaline earth metal ion (such as $Ca^{2+}$ or $Mg^{2+}$) or an aluminium ion; or is coordinated with an organic or inorganic base. Acceptable organic bases include diethanolamine, ethanolamine, N-methylglucamine, triethanolamine, tromethamine and the like. Acceptable inorganic bases include aluminium hydroxide, calcium hydroxide, potassium hydroxide, sodium carbonate and sodium hydroxide.

In this invention, "stereoisomers" refers to diastereoisomers or enantiomers. They are therefore optical isomers. Stereoisomers that are not mirror images of each other are then referred to as "diastereoisomers", and stereoisomers that are non superposable mirror images are referred to as "enantiomers".

A carbon atom bound to four non-identical substitutes is called a "chiral centre".

An equimolar mixture of two enantiomers is called a racemate.

According to one particular embodiment of the invention, a compound according to the invention may satisfy the following formula (Ia):

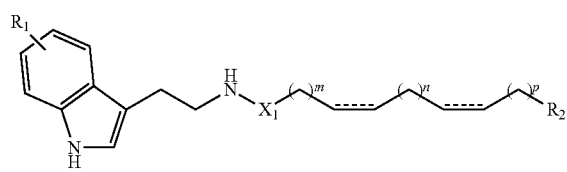
(Ia)

in which:

---- independently represents a single or double bond, $X_1$, $R_1$ and $R_2$ are as defined above, and m represents an integer greater than or equal to 1, and n and p represent, independently of each other, an integer greater than or equal to 0 where $m+n+p+4 \leq 24$ and preferably $8 \leq m+n+p+4 \leq 22$.

More particularly, the compound according to the invention can satisfy the following formulas (Ib) and (Ic):

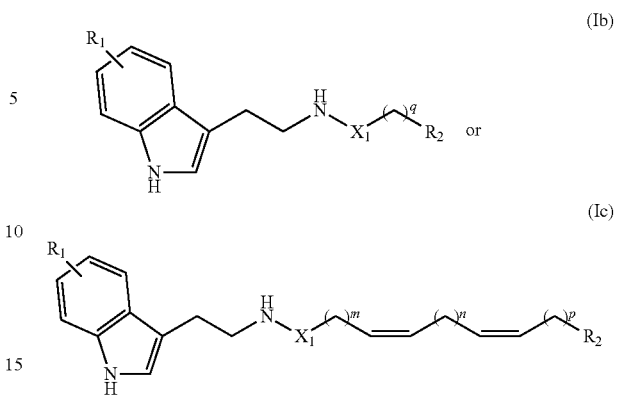

in which:

$R_1$, $R_2$ and $X_1$ are as defined above, q represents an integer between 1 and 24, and preferably between 8 and 22, and m, n and p are as defined above $R_1$ represents a substituent for the indole nucleus, located on any one of the carbon atoms of the indole pattern. It is advantageously a hydrogen atom.

$R_2$ advantageously represents a $CH_3$ or $CH_2OH$ group.

$X_1$ advantageously represents a $CH_2$ group.

In particular, the compounds according to the invention may be chosen from among:

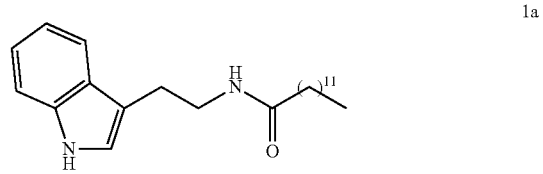
1a

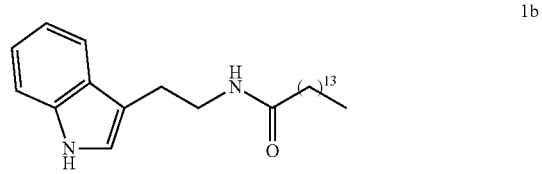
1b

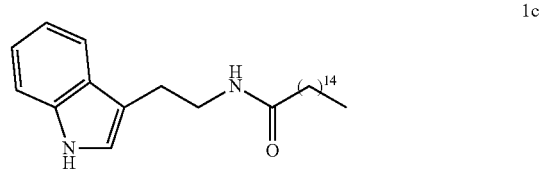
1c

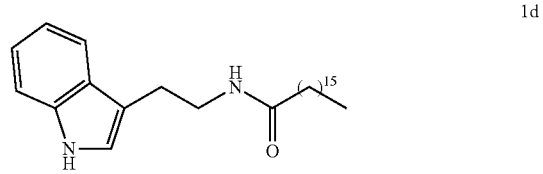
1d

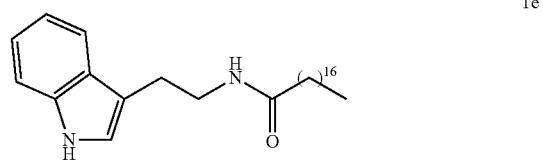
1e

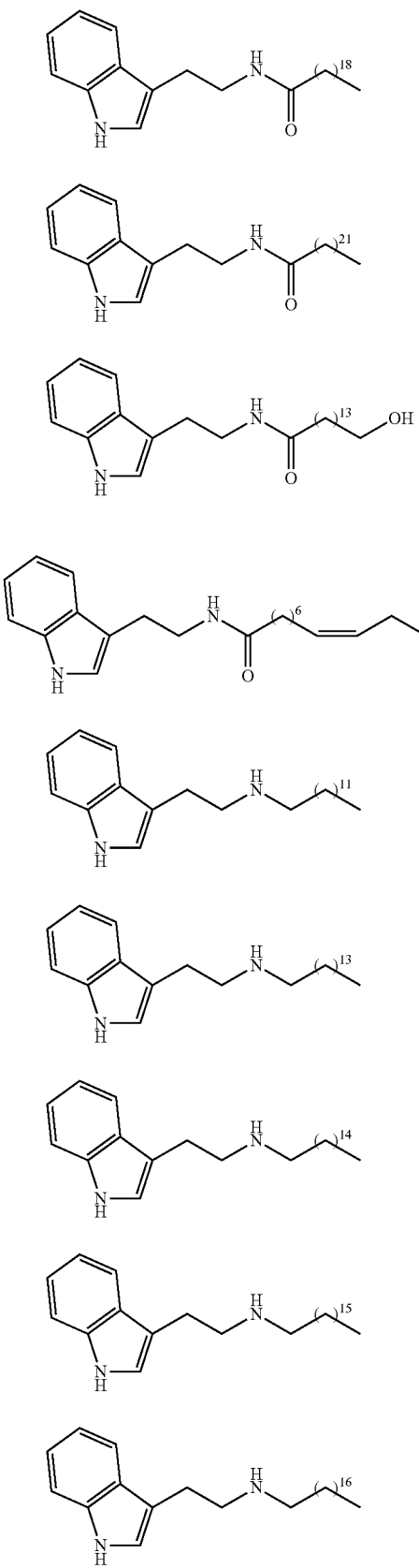
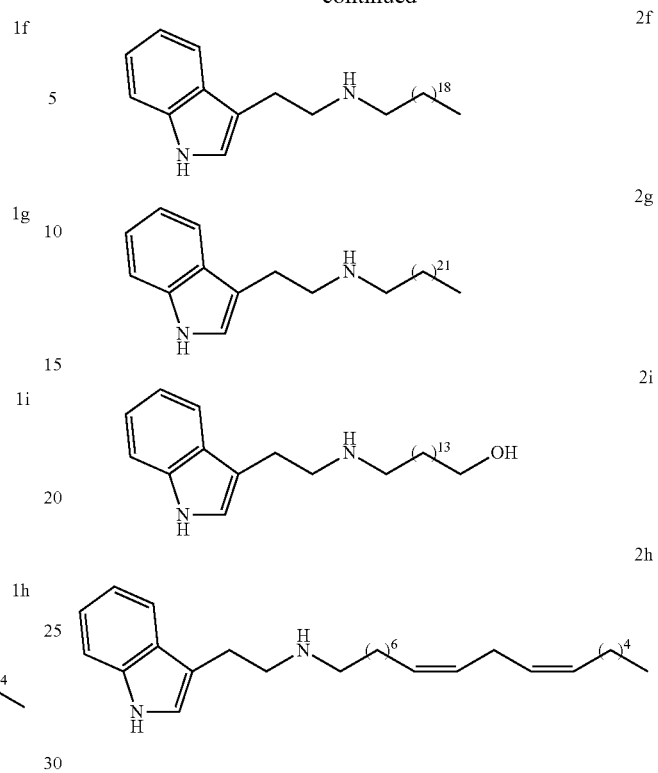

This invention also relates to the use of a compound of formula (I) as defined above for manufacturing a medicine, particularly a neurotrophic or neuroprotective medicine, advantageously intended for the treatment or prevention of neurodegenerative diseases such as Alzheimer's disease, Parkinson's disease, multiple sclerosis or cerebrovascular accidents.

This invention also relates to a method for the treatment or prevention of neurodegenerative diseases such as Alzheimer's disease, Parkinson's disease, multiple sclerosis or cerebrovascular accidents, comprising administration to a patient in need thereof of an effective quantity of a compound of formula (I) as defined above.

Another purpose of this invention is a compound of the following formula (I):

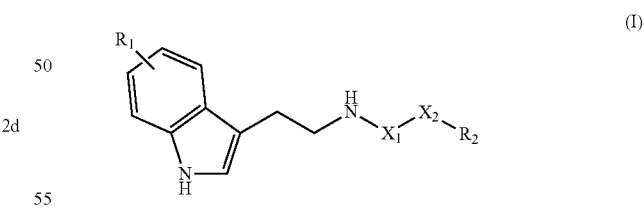

or a pharmaceutically acceptable salt thereof, a stereoisomer or a mixture of stereoisomers in any proportion, particularly a mixture of enantiomers, and particularly a racemate,
in which:
  $X_1$ represents a $CH_2$ or $C=O$ group,
  $X_2$ represents a saturated or unsaturated linear hydrocarbon chain comprising 1 to 24, and preferably 8 to 22, carbon atoms,
  $R_1$ represents a hydrogen atom or an OH or $(C_1-C_6)$alcoxy group such as methoxy, and $R_2$ represents a $CH_3$ or $CH_2OR_3$ group, where $R_3$ represents an atom of hydrogen or a $(C_1-C_6)$alkyl, $CO-(C_1-C_6)$alkyl or $NH-(C_1-C_6)$alkyl group;
excluding compounds with formula:

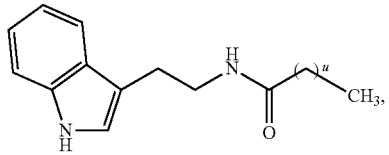

where u=14, 16 to 18 or 20 to 24.

Excluded compounds are described in Wu Y.-C. et al. *J. Nat. Prod.* 2005, 68 (3), 406-408, and Chavez D. et al. *J. Nat. Prod.* 1999, 62 (8), 1119-1122 as new isolated compounds of *Annona atemoya* or *Rollinia mucosa* seeds.

According to one particular embodiment of the invention, a compound according to the invention could satisfy the following formula (Ia):

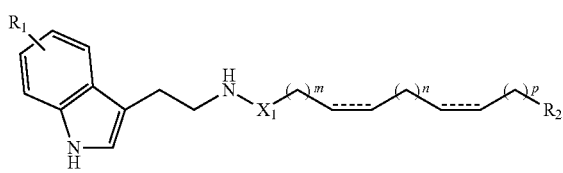

(Ia)

in which:
- - - - independently represents a single or double bond,
$X_1$, $R_1$ and $R_2$ are as defined above, and
m represents an integer greater than or equal to 1, and n and p represent, independently of each other, an integer greater than or equal to 0, where m+n+p+4≤24 and preferably 8≤m+n+p+4≤22.

More particularly, the compound according to the invention may satisfy one of the following formulas (Ib) and (Ic):

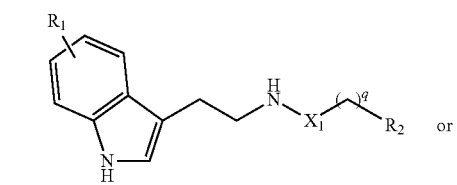

(Ib)

or

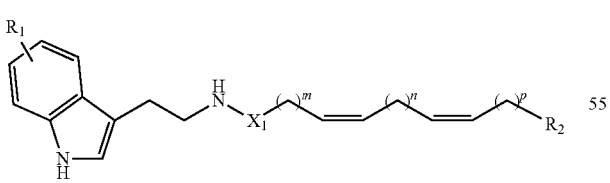

(Ic)

for which:
$R_1$, $R_2$ and $X_1$ are as defined above,
q represents an integer between 1 and 24, and preferably between 8 and 22, and
m, n and p are as defined above.
$R_1$ advantageously represents a hydrogen atom.
$R_2$ advantageously represents a $CH_3$ or $CH_2OH$ group.
$X_1$ advantageously represents a $CH_2$ group.

In particular, the compounds according to the invention may be chosen among the following:

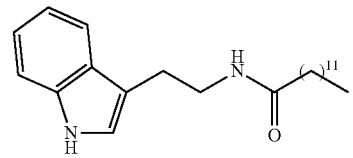
1a

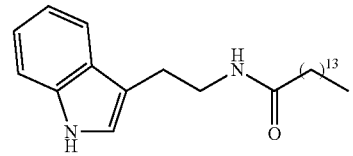
1b

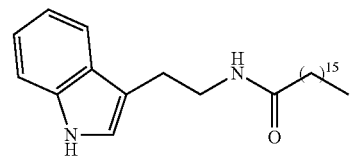
1d

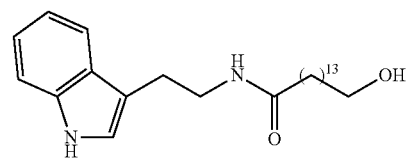
1i

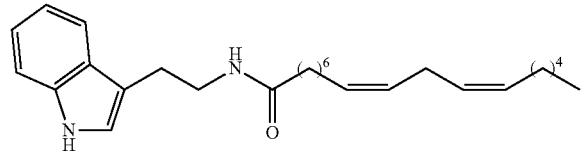
1h

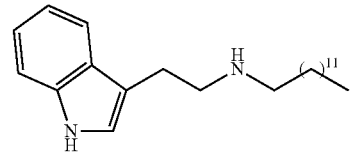
2a

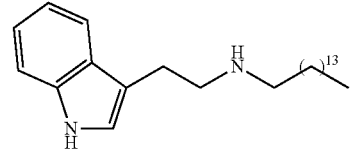
2b

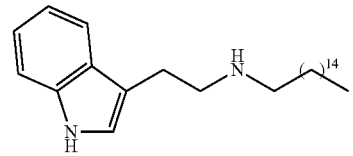
2c

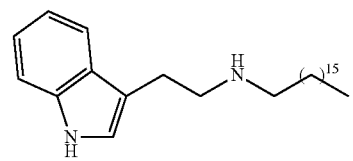
2d

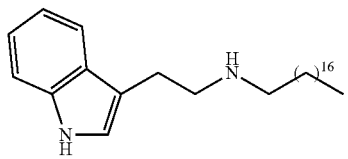
2e

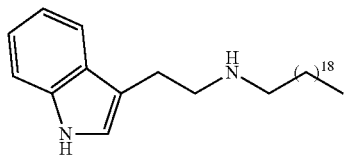
2f

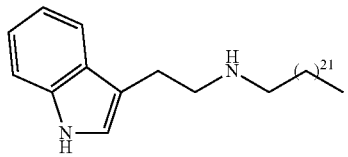
2g

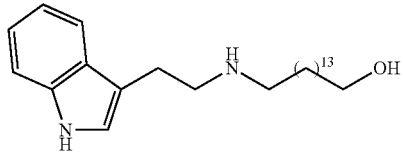
2i

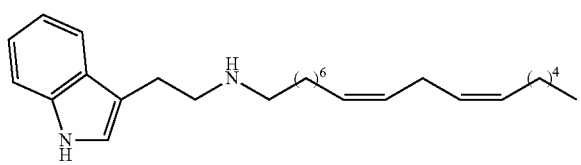
2h

Another purpose of this invention is a pharmaceutical composition comprising at least one compound of formula (I) as described above and a pharmaceutically acceptable carrier.

The compounds according to the invention may be administered by oral, sublingual, parenteral, subcutaneous, intramuscular, intravenous, transdermic, local or rectal pathway, and preferably by oral pathway.

The active principle in pharmaceutical compositions of this invention for oral, sublingual, parenteral, subcutaneous, intramuscular, intravenous, transdermic, local or rectal administration may be administered to animals or human beings, in unit administration forms mixed with classical pharmaceutical carriers. Appropriate unit administration forms comprise forms for oral pathway such as tablets, capsules, powders, pellets and oral solutions or suspensions, sublingual and oral administration forms, parenteral, subcutaneous, intramuscular, intravenous, intranasal or intraocular administration forms and rectal administration forms.

When a solid composition is prepared in the form of tablets, the main active principle is mixed with a pharmaceutical carrier such as gelatine, starch, lactose, magnesium stearate, talc, arabic gum or the like. The tablets may be coated with saccharose or any other appropriate materials or they may be treated so that they have a sustained or delayed activity and so that they continuously release a predetermined quantity of the active principle.

A capsule preparation is obtained by mixing the active principle with a diluent and pouring the mixture obtained in soft or hard capsules.

A preparation in the form of a syrup or elixir may contain the active principle jointly with a sweetener, an antiseptic, and an agent giving taste and an appropriate colouring agent.

Powders or pellets dispersible in water may contain the active principle mixed with dispersing agents or wetting agents, or suspension agents, and with taste regulators or sweeteners.

Rectal administration makes use of suppositories prepared with binders that melt at rectal temperature, for example cocoa butter or polyethylene-glycols.

Parenteral, intranasal or intraocular administrations make use of aqueous suspensions, isotonic saline solutions or sterile and injectable solutions that contain dispersion agents and/or pharmacologically compatible wetting agents.

The active principle may also be formulated in the form of micro-capsules, possibly with one or several additive carriers.

Compounds according to the invention may be used at doses between 0.01 mg and 1000 mg per day, given in a single dose once per day or administered in several doses throughout the day, for example twice per day in equal doses. The dose administered per day is advantageously between 5 mg and 500 mg, and even more advantageously between 10 mg and 200 mg. It may be necessary to use doses outside these ranges, but the person skilled in the art will realise this himself.

According to one particular embodiment, the pharmaceutical composition as defined above may also comprise another active principle, useful particularly in the treatment or prevention of neurodegenerative diseases and advantageously chosen from among acetylcholinesterase inhibitors such as donezepil, galanthamine, rivastigmine, memantine and tacrine; monoamine oxydase inhibitors such as selegiline; O-methyltransferase catecholamine inhibitors such as entacapone; glutamatergic inhibitors such as amantadine and baclofen; cholinergic agonists such as sabcomeline; dopaminergic agonists such as pergolide, cabergoline, ropirinole and pramipexole; neuromediator analogues or precursors such as L-3,4-dihydroxyphenylalanine; and anticholinergics such as trihexyphenidyl and tropatepine.

Another purpose of this invention is a pharmaceutical composition as defined above for use as a medicine, particularly as a neurotrophic or neuroprotective medicine intended advantageously for the treatment or prevention of neurodegenerative diseases such as Alzheimer's disease, Parkinson's disease, multiple sclerosis or cerebrovascular accidents.

Another purpose of this invention is a method for the preparation of a compound of formula (I) as described above, characterised in that it comprises the following steps:

(a) coupling between tryptamine and a compound of the following formula (II):

for which Z represents a free form or an active form of a carboxylic acid function and $R_2$ and $X_2$ are as defined above, to give a compound of the following formula (I-1):

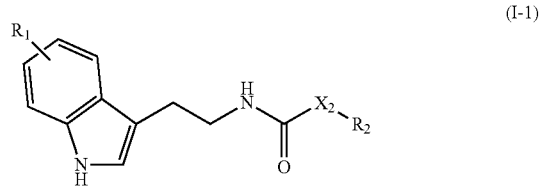

in which $R_1$, $R_2$ and $X_2$ are as defined above, b) optionally reduction of the carbonyl function of the compound of formula (I-1) obtained in step (a) above to give a compound of the following formula (I-2):

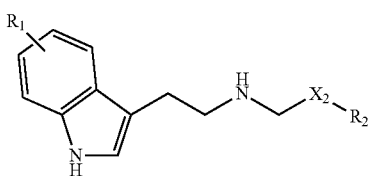

(I-2)

for which $R_1$, $R_2$ and $X_2$ are as defined above, and (c) separation of the compound (I-1) or (I-2) obtained in the previous step from the reaction medium.

Step a:

For the purposes of this invention, a "carboxylic acid function in free form" refers to a $CO_2H$ group.

For the purposes of this invention a "carboxylic acid function in activated form" means a carboxylic acid function modified so as to make it more active towards a nucleophile. These activated forms are well known to those skilled in the art and in particular may be an acid chloride (COCl).

Thus, Z advantageously represents a $CO_2H$ or COCl group.

In particular, the compound of formula (II) may be a commercially available fatty acid or the like when $Z=CO_2H$. If Z represents an activated carboxylic acid function, the compound of formula (II) may be easily obtained from the corresponding commercially available carboxylic acid by activation of the carboxylic acid function using techniques well known to those skilled in the art. Thus, an acid chloride may be obtained particularly by reaction of the corresponding carboxylic acid with oxalyl chloride in the presence of a few drops of dimethylformamide (DMF). This reaction may be carried out in a solvent such as dichloromethane, particularly at ambient temperature.

According to a first particular embodiment of the invention, the compound of formula (II) used comprises a group $Z=CO_2H$ (free acid form). In this case, the coupling reaction will be done in the presence of a coupling agent such as diisopropylcarbodiimide (DIC), dicyclohexylcarbodiimide (DCC), 1-(3-dimethylaminopropyl)-3-ethylcarbodiimide hydrochloride (EDC), carbonyldiimidazole (CDI), 2-H-benzotriazole-1-yl)-1,1,3,3-tetramethyluronium hexafluorophosphate (HBTU), 2-(1H-benzotriazole-1-yl)-1,1,3,3-tetramethyluronium tetrafluoroborate (TBTU) or O-(7-azobenzotriazol-1-yl)-1,1,3,3-tetramethyluronium hexafluorophosphate (HATU), possibly associated with a coupling auxiliary such as N-hydroxy succinimide (NHS), N-hydroxy benzotriazole (HOBt), 3,4-dihydro-3-hydroxy-4-oxo-1,2,3-benzotriazole (HOOBt), 1-hydroxy-7-azabenzotriazole (HAt) or N-hydroxysulfosuccinimide (sulfo NHS). Preferably, coupling will be done in the presence of the EDC/HOBt couple.

This reaction may be done in a solvent such as dichloromethane, particularly at ambient temperature and possibly using a base such as triethylamine.

This first particular embodiment is particularly suitable for the preparation of compounds of formula (I) for which $R_2=CH_2OH$.

According to a second particular embodiment of the invention, the compound used of formula (II) comprises a group Z in the form of an activated carboxylic acid function and more particularly in the form of an acid chloride. In this case, the coupling reaction will advantageously be done in the presence of a base such as triethylamine.

This reaction may be carried out in a solvent such as dichloromethane, particularly at ambient temperature.

This second particular embodiment will advantageously be used when $R_2 \neq CH_2OH$, and particularly when $R_2=CH_2$, because hydroxyl groups (OH) react with oxalyl chloride.

Step b:

This reduction step allows reducing the amide into amine to convert a compound of formula (I) in which $X_1=C=O$ into a compound of formula (I) in which $X_1=CH_2$.

This step will advantageously be done in the presence of a hydride such as $LiAlH_4$. It may be done in a solvent such as tetrahydrofurane.

For the purposes of this invention, a "hydride" refers to a chemical compound capable of releasing H hydride ions to perform a reduction reaction.

Step c:

The final product is separated from the reaction medium using techniques well known to those skilled in the art, for example by extraction, evaporation of the solvent or by precipitation and filtration.

The compound of formula (I) thus obtained can also be purified if necessary using methods well known to those skilled in the art, such as by re-crystallisation if the compound is crystalline, by distillation, by column chromatography on silica gel or by high performance liquid chromatography (HPLC).

This invention will be better understood after reading the following non-limitative examples.

FIGURE

Figure 3:
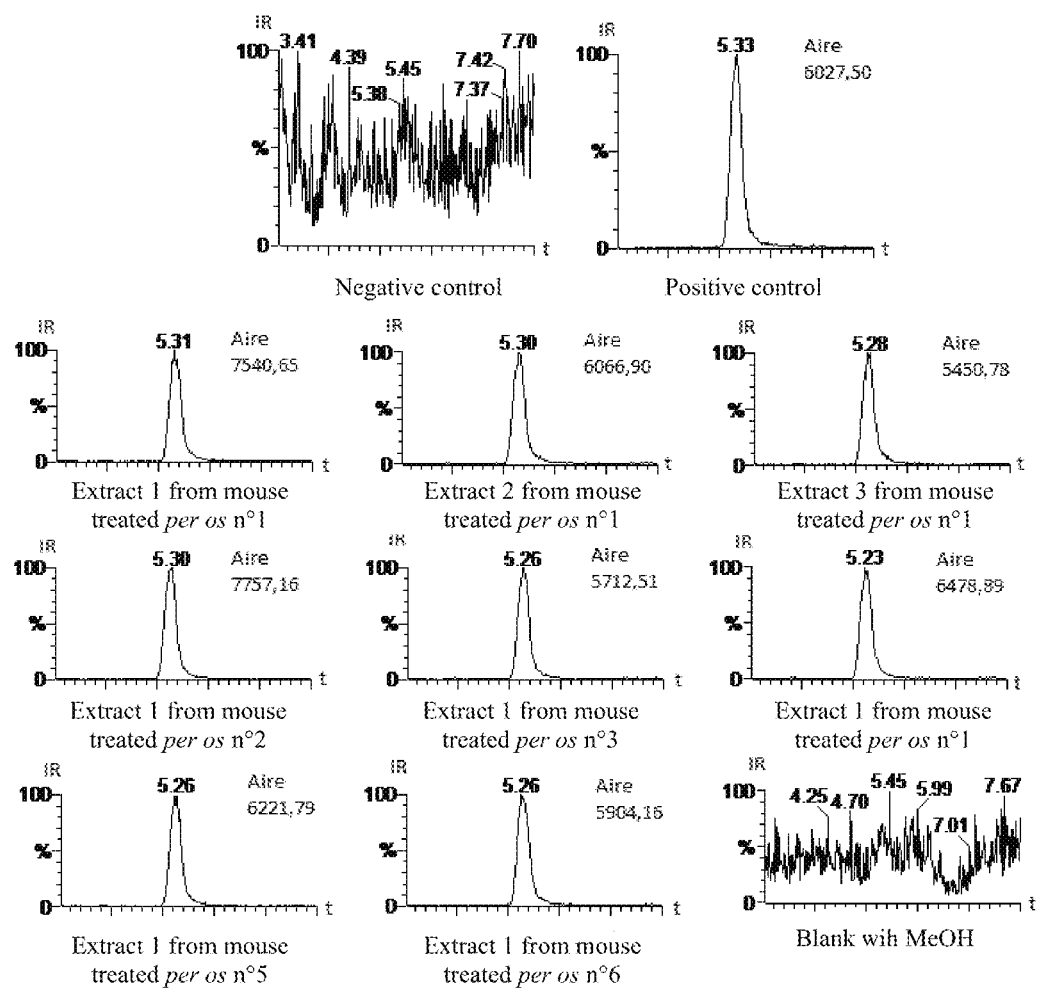
Figure 4:
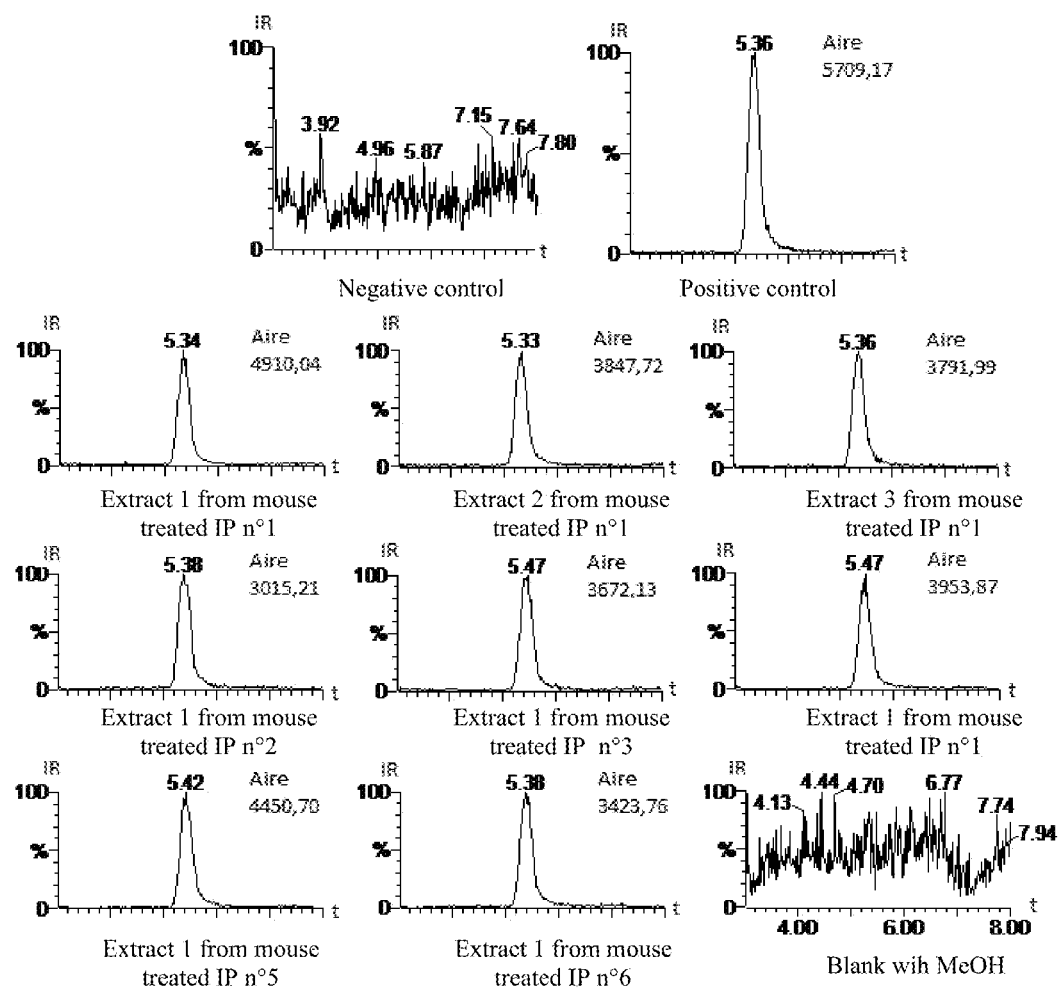

FIG. 3 shows chromatograms (the abscissa shows times in minutes, and the ordinate shows the relative intensity in percent) obtained using HPLC-MS/MS of extracts from the brains of mice used in the experiments in example 2.3, demonstrating the presence or absence of the compound according to invention 2c. FIG. 4 corresponds to chromatograms obtained in the framework of the per os treatment and corresponds to chromatograms obtained in the framework of the intra-peritoneal treatment.

EXAMPLES

1. Synthesis of Compounds According to the Invention 1.1 Synthesis of Compounds of Formula (I) for which $X_1=C=O$ General Synthesis Procedure Starting from Acid Chloride:

Three drops of dry dimethylformamide and oxalyl chloride (1.04 mL, 12 mmol) are added to a solution of fatty acid (2 mmol) in dichloromethane (10 mL) at 0° C. under an inert atmosphere. The mixture is stirred at 0° C. for 1 h. Dichloromethane and excess oxalyl chloride are evaporated under vacuum. The acid chloride thus obtained is dissolved in 5 mL of dry dichloromethane.

Triethylamine (0.55 mL, 2 mmol) is added to a solution of tryptamine (160 mg, 1 mmol) in dichloromethane (10 mL) at 0° C. under an inert nitrogen atmosphere, and then acid chloride in solution in dichloromethane (5 mL) is slowly added. The reaction mixture is stirred at ambient temperature for 2 h. The reaction is hydrolysed, and then extracted with dichloromethane. The organic phase is dried on anhydrous $MgSO_4$ and then concentrated under vacuum. The products are purified on a silica column in a mixture of cyclohexane and ethyl acetate in the proportion 8:2.

N-(2-(1H-indol-3-yl)ethyl)tridecanamide (1a)

Yield: 95%

NMR$^1$H (400 MHz, CDCl$_3$) δ ppm: 0.88 (t, J=6.8 Hz, 3H); 1.25 (m, 17H); 1.58 (m, 5H); 2.09 (t, J=7.2 Hz, 2H); 2.98 (t, J=6.8 Hz, 2H); 3.59 (t, J=6.8 Hz, 1H); 3.62 (t, J=6.8 Hz, 1H); 5.48 (s, 1H); 7.04 (d, J=1.6 Hz, 1H); 7.13 (t, J=7.2 Hz, 1H); 7.22 (t, J=7.2 Hz, 1H); 7.38 (d, J=8.0 Hz, 1H); 7.61 (d, J=8.0 Hz, 1H,); 8.05 (s, 1H).

NMR$^{13}$C (100 MHz, CDCl$_3$) δ ppm: 14.1, 22.5, 25.2, 29.2, 29.3, 29.5, 31.8, 36.8, 39.5, 111.1, 113.1, 118.6, 119.4, 121.8, 122.1, 127.4, 136.4, 173.0.

ESI-MS m/z: 379 ([M+Na]$^+$, 100).

IR cm$^{-1}$: 608, 671, 719, 739, 801, 847, 913, 1009, 1068, 1094, 1130, 1222, 1246, 1271, 1294, 1340, 1377, 1424, 1456, 1470, 1554, 1629, 1650, 2851, 2918, 2955, 3089, 3264, 3387.

N-(2-(1H-indol-3-yl)ethyl)pentadecanamide (1b)

Yield: 77%

NMR$^1$H (400 MHz, CDCl$_3$) δ ppm: 0.88 (t, J=6.8 Hz, 3H); 1.25 (m, 22H); 1.61 (m, 4H); 2.10 (t, J=7.0 Hz, 2H); 2.98 (t, J=6.8 Hz, 2H); 3.58 (t, J=6.4 Hz, 1H); 3.65 (t, J=6.4 Hz, 1H); 5.49 (s, 1H); 7.04 (s, 1H); 7.12 (t, J=7.0 Hz, 1H); 7.22 (t, J=7.8 Hz, 1H); 7.38 (d, J=7.6 Hz, 1H); 7.61 (d, J=8.2 Hz, 1H); 8.04 (s, 1H).

NMR$^{13}$C (100 MHz, CDCl$_3$) δ ppm: 14.1, 22.6, 22.9, 23.7, 25.3, 28.9, 29.2, 29.4, 29.6, 31.8, 36.8, 39.6, 111.2, 112.9, 118.6, 119.3, 122.0, 127.3, 128.7, 130.8, 136.4, 173.1.

ESI-MS m/z: 407 ([M+Na]$^+$, 100).

IR cm$^{-1}$: 607, 718, 739, 801, 931, 1010, 1069, 1094, 1130, 1225, 1297, 1340, 1377, 1425, 1456, 1470, 1555, 1630, 1650, 2850, 2918, 2955, 3267, 3387.

N-(2-(1H-indol-3-yl)ethyl)hexadecanamide (1c)

Yield: 87%

NMR$^1$H (400 MHz, CDCl$_3$) δ ppm: 0.88 (t, J=6.9 Hz, 3H); 1.25 (m,30H); 1.57 (m, 4H); 2.09 (t, J=7.2 Hz, 2H); 2.98 (t, J=6.9 Hz, 2H); 3.60 (t, J=6.6 Hz, 1H); 3.62 (t, J=6.6Hz, 1H); 5.56 (s, 1H); 7.04 (d, J=2.1 Hz, 1H); 7.13 (t, J=0.8 Hz, 1H); 7.22 (t, J=6.9 Hz, 1H); 7.37 (d, J=8.1 Hz, 1H); 7.61 (d, J=7.2 Hz, 1H); 8.06 (s, 1H).

NMR$^{13}$C (100 MHz, CDCl$_3$) δ ppm: 14.1, 22.7, 25.2, 25.3, 25.7, 26.9, 29.1, 29.3, 29.4, 29.5, 29.6, 29.7, 31.9, 33.4, 36.9, 39.7, 111.2, 113.0, 118.7, 119.4, 122.0, 122.1, 127.4, 136.4, 173.1.

ESI-MS m/z: 421 ([M+Na]$^+$, 100).

IR cm$^{-1}$: 608, 718, 739, 801, 1011, 1094, 1225, 1293, 1340, 1377, 1456, 1553, 1630, 2850, 2918, 3267, 3387.

N-(2-(1H-indol-3-yl)ethyl)heptadecanamide (1d)

Yield: 93%

NMR$^1$H (400 MHz, CDCl$_3$) δ ppm: 0.88 (t, J=6.6 Hz, 3H); 1.25 (m, 26H); 1.57 (m, 2H); 2.09 (t, J=7.6 Hz, 2H); 2.98 (t, J=6.8 Hz, 2H); 3.60 (t, J=6.6 Hz, 1H); 3.62 (t, J=6.6 Hz, 1H); 5.49 (s, 1H); 7.04 (d, J=2.1 Hz, 1H); 7.13 (t, J=7.6 Hz, 1H); 7.21 (t, J=7.6Hz, 1H); 7.38 (d, J=8.0 Hz, 1H); 7.61 (d, J=8 Hz, 1H); 8.09 (s, 1H).

NMR$^{13}$C (100 MHz, CDCl$_3$) δ ppm: 14.1, 22.7, 25.4, 25.7, 29.3, 29.4, 29.6, 29.7, 31.9, 36.9, 39.6, 111.2, 113.1, 118.7, 119.5, 121.9, 122.2, 127.3, 136.4, 173.1.

ESI-MS m/z: 435 ([M+Na]$^+$, 100).

IR cm$^{-1}$: 717, 739, 800, 1010, 1067, 1094, 1225, 1300, 1339, 1377, 1423, 1456, 1471, 1552, 1629, 1649, 2850, 2918, 3267, 3393.

N-(2-(1H-indol-3-yl)ethyl)octadecanamide (1e)

Yield: 95%

NMR$^1$H (400 MHz, CDCl$^3$) δ ppm: 0.88 (t, J=6.9 Hz, 3H); 1.25 (m, 27H); 1.57 (m, 2H); 2.09 (t, J=7.2 Hz, 2H); 2.98 (t, J=6.6 Hz, 2H); 3.60 (t, J=6.3 Hz, 1 H); 3.62 (t, J=6.3 Hz, 1H); 5.45 (s, 1H); 7.03 (d, J=2.1 Hz, 1H); 7.13 (t, J=7.8 Hz, 1H); 7.21 (t, J=7.8 Hz, 1H); 7.38 (d, J=8.1 Hz, 1H); 7.61 (d, J=7.2 Hz, 1H); 8.07 (s, 1H).

NMR$^{13}$C (100 MHz, CDCl$^3$) δ ppm: 14.1, 22.7, 25.4, 25.7, 29.3, 29.4, 29.5, 29.6, 29.7, 31.9, 36.9, 39.6, 111.2, 113.2, 118.8, 119.5, 121.9, 122.2, 127.4, 136.4, 173.1.

ESI-MS m/z: 449 ([M+Na]$^+$(100).

IR cm$^{-1}$: 609, 718, 739, 800, 1013, 1094, 1224, 1298, 1339, 1377, 1424, 1456, 1553, 1629, 1649, 2850, 2918, 3267, 3392.

N-(2-(1H-indol-3-yl)ethyl)icosanamide (1f)

Yield: 50%

NMR$^1$H (400 MHz, CDCl$_3$) δ ppm: 0.88 (t, J=6.8 Hz, 3H); 1.25 (m, 30H); 1.57 (m, 2H); 2.09 (t, J=7.6 Hz, 2H); 2.98 (t, J=6.8 Hz, 2H); 3.60 (t, J=6.4 Hz, 1H); 3.62 (t, J=6.4 Hz, 1H); 5.05 (s, 1H); 7.04 (s, 1H); 7.13 (t, J=8.0 Hz, 1H); 7.21 (t, J=7.6 Hz, 1H); 7.38 (d, J=8.0 Hz, 1H); 7.61 (d, J=7.6 Hz, 1H); 8.10 (s, 1H).

NMR$^{13}$C (100 MHz, CDCl$_3$) δ ppm: 14.1, 22.7, 25.4, 25.7, 29.3, 29.4, 29.5, 29.7, 31.9, 33.7, 36.9, 39.6, 111.2, 113.1, 118.7, 119.5, 121.9, 122.2, 136.6, 173.1.

ESI-MS m/z: 477 ([M+Na]$^+$ (100).

IR cm$^{-1}$: 669, 718, 739, 799, 913, 1012, 1066, 1095, 1222, 1299, 1339, 1377, 1424, 1456, 1472, 1552, 1629, 1649, 2850, 2917, 3269, 3394.

N-(2-(1H-indol-3-yl)ethyl)tricosanamide (1g)

Yield: 88%

NMR$^1$H (400 MHz, CDCl$_3$) δ ppm: 0.88 (t, J=6.6 Hz, 3H); 1.25 (m, 38H); 1.57 (m, 2H); 2.09 (t, J=7.2 Hz, 2H); 2.98 (t, J=6.4 Hz, 2H); 3,60 (t, J=6.4 Hz, 1H); 3.62 (t, J=6,4 Hz, 1H); 5.47 (s, 1H); 7.04 (d, J=2.0 Hz, 1H); 7.13 (t, J=7.6 Hz, 1H); 7.21 (t, J=7.6 Hz, 1H); 7.38 (d, J=8.4 Hz, 1H); 7.61 (d, J=8.0 Hz, 1H); 8.02 (s, 1H).

NMR$^{13}$C (100 MHz, CDCl$_3$) δ ppm: 14.1, 22.7, 25.4, 25.7, 29.3, 29.4, 29.5, 29.7, 31.9, 33.7, 36.9, 39.6, 111.2, 113.1, 118.7, 119.5, 121.9, 122.2, 136.6, 173.1.

ESI-MS m/z: 497 ([M+Na]$^+$, 100).

IR cm$^{-1}$: 560, 580, 612, 719, 738, 800, 983, 1093, 1225, 1342, 1377, 1462, 1472, 1564, 1628, 2848, 2917, 2959, 3258, 3396

(8Z, 11Z)-N-(2-(1H-indol-3-yl)ethyl)heptadeca-8,11-dienamide (1h)

Yield: 81%

NMR$^1$H (400 MHz, CDCl$_3$) δ ppm: 0.90 (t, J=6.8 Hz, 3H); 1.25 (m, 14H); 1.59 (t, J=6.8 Hz, 2H); 2.06 (m, 4H); 2.10 (t. J=7.2 Hz, 2H); 2.79 (t, J=6.4 Hz, 2H), 2.98 (t, J=6,4 Hz, 2H); 3.59 (t, J=6.4 Hz, 1 H); 3,62 (t, J=6,4 Hz, 1H); 5.37 (m, 4H); 5.63 (s, 1H); 7.00 (d, J=1,6 Hz, 1H); 7.12 (t, J=7.6 Hz, 1H); 7.21 (t, J=7.6 Hz, 1H); 7.37 (d, J=8.0 Hz, 1H); 7.60 (d, J=7.6 Hz, 1H); 8.47 (s, 1H).

NMR¹³C (100 MHz, CDCl₃) δ ppm: 14.0, 22.5, 25.3, 25.6, 25.7, 27.1, 29.1, 29.2, 29.3, 29.4, 29.6, 31.5, 36.8, 39,7, 111.3, 112.8, 118.6, 119.3, 122.0, 127.3, 127.8, 128.0, 130.0, 130.2, 136.4, 173.2.

ESI-MS m/z: 445 ([M+Na]⁺, 100).

IR cm⁻¹: 560, 580, 608, 719, 739, 801, 931, 1011, 1069, 1094, 1126, 1225, 1269, 1299, 1340, 1377, 1425, 1456, 1555, 1629, 1650, 2851, 2920, 3010, 3264, 3386.

General Synthesis Procedure Starting from a Free Carboxylic Acid:

Triethylamine (0.83 mL, 6 mmol), EDC (768 mg, 4 mmol) and HOBt (405 mg, 3 mmol) are added to a solution of tryptamine (320 mg, 2 mmol) and carboxylic acid (518 mg, 2 mmol) in dichloromethane (40 mL). The mixture is stirred overnight at ambient temperature under an inert nitrogen atmosphere. The reaction is hydrolysed and then extracted with dichloromethane and washed with an aqueous solution saturated with NH₄Cl. The organic phase is dried on anhydrous MgSO₄ and concentrated under vacuum. The product is purified on a silica column in a mixture of dichloromethane and methanol in proportion 95:5.

N-(2-(1H-indol-3-yl)ethyl)-15-hydroxypentadecanamide (1i)

Yield: 60%

NMR¹H (400 MHz, CDCl₃) δ ppm: 1.25 (m, 22H); 1.57 (m, 4H); 2.09 (t, J=7.2 Hz, 2H); 2.98 (t, J=6.8 Hz, 2H); 3.59-3.65 (m, 4H); 5.48 (s, 1H); 7.04 (d, J=1.6 Hz, 1H); 7.13 (t, J=7.6 Hz, 1H); 7.22 (t, J=8.0 Hz, 1H); 7.38 (d, J=8.0 Hz, 1H); 7.61 (d, J=8.0 Hz, 1H); 8.06 (s, 1H).

NMR¹³C (100 MHz, CDCl₃) δ ppm: 24.8, 25.4, 25.7, 26.3, 29.3, 29.4, 29.5, 30.4, 39.6, 63.1, 105.1, 111.2, 118.5, 118.8, 119.5, 121.9, 122.3, 127.4, 183.4.

ESI-MS m/z: 423 ([M+Na]⁺, (100).

IR cm⁻¹: 606, 704, 727, 741, 758, 974, 1012, 1026, 1057, 1109, 1166, 1224, 1267, 1357, 1375, 1457, 1556, 1629, 1669, 1982, 2037, 2849, 2917, 3275, 3394.

1.2. Synthesis of Compounds of Formula (I) for Which X=CH₂

General Procedure:

LiAlH₄ (304 mg, 8 mmol) is slowly added in small portions to a solution of amide (as prepared previously) (1 mmol) in THF (10 mL) at 0° C. under an inert nitrogen atmosphere. The mixture is then refluxed for 2 h. After cooling, the reaction is gently hydrolysed by 1 mL of water, and a solution of 1M NaOH is then added drop by drop until a white precipitate is obtained. The mixture is filtered on celite, washed with ethyl acetate and then dried on anhydrous MgSO₄ and concentrated at low pressure.

N-(2-(1H-indol-3-yl)ethyl)tridecan-1-amine (2a)

Yield: 84%

NMR¹H (300 MHz, CDCl₃) δ ppm: 0.88 (t, J=6.9 Hz, 3H); 1.25 (m, 21H); 1.46 (m, 2H); 2.62 (t, J=7.2 Hz, 2H); 2.97 (m, 4H); 7.04 (d, J=2.1 Hz, 1H); 7.12 (td, J=0.9 Hz, J=7.8 Hz, 1H); 7.20 (td, J=1.2 Hz, J=7.2 Hz, 1H); 7.36 (d, J=7.8 Hz, 1H); 7.64 (d, J=7.8 Hz, 1H); 8.10 (s, 1H)

NMR¹³C (75 MHz, CDCl₃) δ ppm: 14.1, 22.7, 25.8, 27.4, 29.3, 29.6, 29.7, 30.1, 32.0, 50.0, 111.1, 114.2, 118.9, 119.2, 121.8, 122.0, 127.5, 136.4.

ESI-MS m/z: 343 ([M+H]⁺, 100).

IR cm⁻¹: 565, 592, 611, 722, 739, 804, 842, 886, 914, 1010, 1078, 1104, 1221, 1309, 1341, 1358, 1376, 1453, 1467, 1504, 1553, 1622, 2849, 2916, 3063, 3139, 3275, 3387.

N-(2-(1H-indol-3-yl)ethyl)pentadecan-1-amine (2b)

Yield: 83%

NMR¹H (300 MHz, CDCl₃) δ ppm: 0.89(t, J=6.9 Hz, 3H); 1.26 (m, 24H); 1.46 (m, 2H); 2.62 (t, J=7.2Hz,2H); 2.97 (m, 4H); 7.04 (d, J=1.8Hz,1H); 7.12 (td, J=1.2Hz, J=7.8 Hz, 1H); 7.20 (td, J=1.2 Hz, J=8.1 Hz, 1H); 7.36 (d, J=7.8 Hz, 1H); 7.64 (d, J=7.5Hz, 1H); 8.18 (s, 1H).

NMR¹³C (75 MHz, CDCl₃) δ ppm: 14.1, 22.7, 25.8, 27.4, 27.5, 29.4, 29.6, 29.7, 30.1, 31.9, 50.0, 111.1, 114.1, 117.4, 118.9, 119.2, 121.8, 122.0, 128.4, 133.4.

ESI-MS m/z: 371 ([M+H]⁺, 100).

IR cm⁻¹: 592, 611, 721, 739, 805, 874, 1011, 1104, 1222, 1341, 1454, 1630, 2649, 2916, 3387.

N-(2-(1H-indol-3-yl)ethyl)hexadecan-1-amine (2c)

Yield: 50%

NMR¹H (300 MHz, CDCl₃) δ ppm: 0.88 (t, J=6.9 Hz, 3H); 1.25 (m, 26H); 1.47 (m, 2H); 2.61 (t, J=7.2 Hz, 2H); 2.97 (m, 4H); 7.04 (d, J=1.8 Hz, 1H); 7.11 (td, J=1.2 Hz, J=8.1 Hz, 1H); 7.19(td, J=1.2 Hz, J=8.1 Hz, 1H); 7.36 (d, J=8.1 Hz, 1H); 7.62 (d, J=7.8 Hz, 1H); 8.21 (s, 1H).

NMR¹³C (75 MHz, CDCl₃) δ ppm: 14.1, 22.7, 25.6, 27.3, 29.3, 29.5, 29.6, 29.7, 29.8, 30.0, 31.9, 50.0, 111.1, 113.8, 118.8, 119.2, 122.0, 127.4, 136.4.

ESI-MS m/z: 385 ([M+H]⁺, 100).

IR cm⁻¹: 565, 592, 611, 721, 739, 784, 803, 842, 886, 910, 1011, 1105, 1222, 1341, 1376, 1454, 1467, 1621, 2849, 2916, 3053, 3139.

N-(2-(1H-indol-3-yl)ethyl)heptadecan-1-amine (2d)

Yield: 90%

NMR¹H (200 MHz, CDCl₃) δ ppm: 0.88 (t, J=6.9 Hz, 3H); 1.25 (m, 28H); 1.46 (m, 2H); 2.61 (t, J=7.2 Hz, 2H); 2.97 (m, 4H); 7.05 (d, J=2.1 Hz, 1H); 7.12 (t, J=7.8 Hz, 1H); 7.20 (t, J=7.5 Hz, 1H); 7.37 (d, J=8.1 Hz, 1H); 7.64 (d, J=7.8 Hz, 1H); 8.05 (s, 1H).

NMR¹³C (SOMHz, CDCl3) δ ppm: 14.1, 22.7, 25.9, 27.4, 29.3, 29.6, 29.7, 30.2, 31.9, 50.0, 111.1, 114.2, 118.9, 119.2, 121.8, 122.0, 127.5, 136.4.

ESI-MS m/z: 399 (N+H⁺, 100).

IR cm⁻¹: 565, 592, 612, 721, 739, 805, 841, 871, 891, 1011, 1074, 1105, 1223, 1342, 1358, 1376, 1454, 1466, 1505, 1622, 2849, 2916, 3064, 3141.

N-(2-(1H-indol-3-yl)ethyl)octadecan-1-amine (2e)

Yield: 52%

NMR¹H (300 MHz, CDCl₃) δ ppm: 0.88 (t, J=6.9 Hz, 3H); 1.25 (m, 30H); 1.46 (m, 2H); 2.62 (t, J=7.2 Hz, 2H); 2.98 (m, 4H); 7.04 (d, J=1.8 Hz, 1 H); 7.12 (t, J=7.8 Hz, 1H); 7.20 (t, J=7.8 Hz, 1H); 7.36 (d, J=8.1 Hz, 1H); 7.63 (d, J=7.8 Hz, 1H); 8.11 (s, 1H).

NMR¹³C (75 MHz, CDCl₃) δ ppm: 14.1, 22.7, 25.4, 27.4, 29.4, 29.7, 30.0, 32.0, 49.9, 111.1, 114.0, 118.9, 119.2, 121.8, 121.9, 122.0, 136.4.

ESI-MS m/z: 413 (N+H⁺, 100).

IR cm⁻¹: 563, 577, 600, 735, 805, 1010, 1125, 1223, 1339, 1455, 1619, 2848, 2916, 3417.

N-(2-(IH-indol-3-yl(ethyl)icosan-1-amine (2f)

Yield: 74%

NMR¹H (300 MHz, CDCl₃) δ ppm: 0.88 (t, J=6.9 Hz, 3H); 1.25 (m, 34H); 1.54 (m, 2H); 2.62 (t, J=7.2 Hz, 2H); 2.97 (m, 4H); 7.04 (d, J=2.1 Hz, 1H); 7.11 (t, J=7.8 Hz, 1H); 7.19 (t, J=7.8 Hz, 1H); 7.36 (d, J=7.8 Hz, 1H); 7.63 (d, J=8.1 Hz, 1H); 7.98 (s, 1H).

NMR$^{13}$C (75 MHz, CDCl$_3$) δ ppm: 14.1, 22.7, 25.8, 27.4, 29.4, 29.7, 30.1, 31.9, 49.9, 111.1, 114.1, 119.1, 119.6, 121.8, 122.0, 127.4, 136.4.

ESI-MS m/z: 441 (N+H$^+$, 100).

IR cm$^{-1}$: 562, 572, 592, 609, 720, 740, 806, 868, 1011, 1104, 1221, 1341, 1455, 1626, 2849, 2916, 3244.

N-(2-(1H-indol-3-yl)ethyl)tricosan-1-amine (2g)

Yield: 52%

NMR$^1$H (300 MHz, CDCl$_3$) δ ppm: 0.88 (t, J=6.8 Hz, 3H); 1.25 (m, 40H); 1.47 (m, 2H); 2.63 (t, J=7.6 Hz, 2H); 2.99 (m, 4H); 7.06 (s, 1H); 7.12 (t, J=7.6 Hz, 1H); 7.20 (t, J=7.6 Hz, 1H); 7.36 (d, J=8.0 Hz, 1H); 7.62 (d, J=8.0 Hz, 1H); 8.03 (s, 1H).

NMR$^{13}$C (75 MHz, CDCl$_3$) δ ppm: 14.1, 22.7, 25.6, 27.3, 29.2, 29.3, 29.4, 29.5, 29.7, 31.9, 49.8, 111.1, 113.9, 118.9, 119.3, 122.0, 127.4, 136.4.

ESI-MS m/z: 483 ([M+H]$^+$, 100).

IR cm$^{-1}$: 577, 668, 720, 735, 746, 805, 1091, 1215, 1463, 1619, 2849, 2916, 3418.

(8Z, 11Z)-N-(2-(IH-indol-3-yl)ethyl)heptadeca-8,11-dienamine (2h)

Yield: 52%

NMR$^1$H (300 MHz, CDCl$_3$) δ ppm: 0.89 (t, J=6.8 Hz, 3H); 1.25 (m, 14H); 1.49 (m, 2H); 2.04 (m, 4H); 2.64 (t, J=7.2 Hz, 2H), 2.77 (t, J=6.4 Hz, 2H), 3.00 (m, 4H); 5.34 (m, 4H); 7.04 (s, 1H); 7.11 (t, J=7.6 Hz, 1H); 7.19 (t, J=7.2 Hz, 1H); 7.36 (d, J=8.0 Hz, 1H); 7.63 (d, J=7.6Hz, 1H); 8.10 (s, 1H).

NMR$^{-}$C (75 MHz, CDCl$_3$) δ ppm: 14.1, 22.6, 25.5, 25.6, 27.2, 27.3, 29.2, 29.3, 29.5, 29.6, 29.7, 31.5, 49.8, 111.1, 113.8, 118.9, 119.3, 121.9, 122.0, 127.4, 127.9, 128.0, 130.1, 130.2, 136.4.

ESI-MS m/z: 409 ([M+H]$^+$, 100).

IR cm$^{-1}$: 625, 738, 803, 1010, 1108, 1231, 1354, 1456, 1620, 2853, 2923, 3009, 3415.

N-(2-(1H-indol-3-yl)ethyl)-15-hydroxypentadecanamine (2i)

Yield: 71%

NMR$^1$H (300 MHz, CDCl$_3$) δ ppm: 1.24 (m, 24H); 1.47 (m, 4H); 2.62 (t, J=7.6 Hz, 2H); 2.97 (m, 4H); 3.64 (t, J=6.8 Hz, 2H); 7.04 (d, J=1.6 Hz, 1H); 7.11 (t, J=7.6 Hz, 1H); 7.20 (t, J=7.6 Hz, 1H); 7.36 (d, J=8.0 Hz, 1H); 7.63 (d, J=8.0 Hz, 1H); 8.03 (s, 1H).

NMR$^1$C (75 MHz, CDCl$_3$) δ ppm: 25.7, 25.8, 27.4, 29.4, 29.5, 30.1, 32.8, 50.0, 63.0, 111.1, 114.2, 118.9, 119.3, 121.8, 122.0, 124.5, 136.4.

ESI-MS m/z: 387 ([M+H]$^+$, 100).

IR cm$^{-1}$: 587, 669, 727, 740, 760, 974, 1010, 1024, 1044, 1108, 1149, 1216, 1355, 1374, 1457, 1466, 1668, 2848, 2923, 3299, 3425.

2. Biological Results

AsH indicated in the preamble, there is a real need to find new small and only slightly hydrophilic molecules to pass through the blood-brain barrier and being capable of miming the effect of neurotrophines.

In vitro, the neurotrophic activity of neuronal growth factors is characterised by their capacity firstly to promote neuron survival and secondly to stimulate neuron maturing.

One innovative approach used in the search for small molecules miming neurotrophic activities consists of studying neuroprotective and neuritogenic properties of studied compounds separately, since the compounds of interest must have the two activities. Measurement of neuritogenesis is a morphological criterion representative of the state of neuron maturity.

Antioxidant compounds also have a neuroprotective capacity. This is why it is also interesting to evaluate the anti-oxidant capacity of compounds according to the invention.

2.1 Neuroprotective and Neuritogenic Activities of Compounds According to the Invention Operating Procedure Dissection. Dissection consists of extracting embryos from the uterus of a rat after fifteen days of gestation. The brain of each embryo is then dissected under magnifying binoculars in order to extract the ventral mesencephalus.

Seeding. Mesencephalons are grouped in a flask containing 2 mL of L15 medium and then mechanically dissociated (30 repeat operations), 5 mL of L15 medium are added. The suspension is allowed to stand for 8 minutes. The 5 mL float is then recovered in a new flask and the cells are dissociated again (30 repeat operations). 5 mL of L15 is added again and the suspension is left to stand for 8 minutes. The 5 mL float is added to the previous float. The cells thus extracted are then centrifuged for 5 minutes at 1000 rpm$^{-1}$. The cell sediment is dissolved in a Neurobasal medium supplemented with 1% of B27, 1% of glutamine and 1% of a mixture of penicillin and streptomycin. The cells are then seeded at an appropriate dilution (0.6 embryos per well in 24-well plates and 0.4 per well in 48-well plates). The cultures are incubated at 37° C. in a wet atmosphere enriched with 5% $CO_2$ in 24-well or 48-well plates.

Treatment. After 24 hours, two-thirds of the medium in each well is replaced by a new medium enriched with the product to be tested at the appropriate dilution. The medium is replaced in the same way after 4 days of culture.

Immunohistochemistry. After 8 days culture, the cells are fixed by a solution of 4% formaldehyde and then washed three times with PBS. The cells are then submitted to anti-tyrosine hydroxylase (TH) immunohistochemistry, developed by a secondary antibody coupled to a fluorophore emitting in the red (Cy3).

Analyses. Neuroprotection is evaluated by counting positive TH neurons with 10 fields per well directly under an inverted fluorescence microscope, reported as a percentage of the untreated control. Experiments are done on three wells per condition. Three independent experiments are done under these conditions. The total neuritic length per cell is calculated using Explora Nova's Neurite Outgrowth software on 60 to 100 neurons photographed independently per condition.

Results

The ventral mesencephalon contains dopaminergic neurons originating from the black substance that degenerate in Parkinson's disease, and the neurons present in the ventral tegmental area.

Primary cultures of embryo ventral mesencephalon may be made after extraction and dissection of the embryos, collection and dissociation of ventral mesencephalons and seeding of the cellular suspension in multi-well plates.

The primary cultures of ventral mesencephalon are mixed cultures. Two neural populations are represented in them, neurons and glia. The neurons present in culture are essentially GABAergic (≈94%) along with dopaminergic neurons (≈3%) and serotoninergic neurons (≈3%). Glia is essentially astrocytary, there are also oligodendrocytes and microglia (≈3%) in smaller proportions. Other non-neural cell types are also present in very small proportions such as erythrocytes, fibroblasts and endothelial cells.

The different cellular populations may be identified by immunocytochemistry of specific markers. Dopaminergic neurons are identified by tyrosine hydroxylase marking.

Previous studies describe spontaneous, progressive and specific degeneration of dopaminergic neurons in primary cultures of ventral mesencephalon (Guerreiro S. et al. *Mol. Pharmacol.* 2008, 74, 980-989).

The number of dopaminergic neurons (TH+ neurons) gradually reduces with time, while the total number of neurons is not affected. This observation was exploited as an in vitro model of neuron death in Parkinson's disease in the search for neuroprotective compounds.

Under these conditions, the remaining neuron fibres are not affected and the neuritogenesis may be observed and quantified. Therefore, this model is particularly interesting in our study because it makes it possible to obtain the two expected results, namely quantification of neuroprotection and neuritogenesis, in a single experiment.

The neurotrophic potential of our compounds was evaluated by double screening including an estimate of the neuroprotective potential and the capability of stimulating neuritic growth.

Primary cultures of ventral mesencephalon of rat embryos after 15.5 days of gestation under conditions causing spontaneous death of dopaminergic neurons, are maintained in the presence or absence of the compounds to be tested for 8 days. After fixing, the cultures are submitted to immunocytochemistry directed against tyrosine hydroxylase, a specific marker of dopaminergic neurons.

The neuroprotective potential of each compound is then estimated by counting the number of remaining neurons ($TH^+$ neurons) under a fluorescence microscope. The results for the different treatments are expressed as a percentage of the number of neurons remaining relative to untreated cultures (Control).

Neuritogenesis is quantified by measuring the total neuritic length per dopaminergic neuron (neuritic length/$TH^+$ neuron) using an image analyser on a minimum of sixty photographed neurons per condition (10-30% of all dopaminergic neurons).

All experiments were done by comparison with a positive control, dibutyryl-AMP cyclic (db-AMPc) (Mourlevat S. et al. *Mol. Pharmacol.* 2003, 64 (3), 578-586).

Tests of significativity were made to compare data with each other, in order to differentiate the probabilities obtained for the two types of activities; we will use the notations $P_P$ and $P_N$ for probabilities concerning protective activity and neuritogenic activity respectively. $P_{P/N}$ will be used when the given probability applies to the two activities.

Compounds according to the invention were tested at 1, 10, 100 and 1000 nM, with an effect observed at 10 nM, the compounds in this series being inactive or toxic respectively at lower and higher concentrations. The results obtained are given in Table 1 below.

TABLE 1

| Product (10 nM) | $X_1$ | $X_2$ | $R_2$ | $TH^+$ neurons | Neuritic length/$TH^+$ neuron |
|---|---|---|---|---|---|
| | | | | % relative to control ± SEM[a] | |
| Control | — | — | — | 100 ± 1.9 | 100 ± 2.9 |
| db-AMPc | — | — | — | 149.9 ± 3.6 | 333.1 ± 8.7** |
| 1c | C=O | $(CH_2)_{14}$ | $CH_3$ | 121.3 ± 3.2** | 168.6 ± 11.5** |
| 1f | C=O | $(CH_2)_{18}$ | $CH_3$ | 121.8 ± 2.0** | 147.4 ± 7.0** |
| 2c | $CH_2$ | $(CH_2)_{14}$ | $CH_3$ | 131.9 ± 4.7** | 197.0 ± 14.0** |
| 2e | $CH_2$ | $(CH_2)_{16}$ | $CH_3$ | 129.9 ± 3.5** | 157.3 ± 10.3** |
| 2f | $CH_2$ | $(CH_2)_{18}$ | $CH_3$ | 128.9 ± 3.4** | 132.6 ± 6.2* |
| 2g | $CH_2$ | $(CH_2)_{21}$ | $CH_3$ | 129.6 ± 3.5** | 141.2 ± 5.0** |
| 2h | $CH_2$ | $\Delta^b$ | $CH_3$ | 137.5 ± 8.0** | 156.7 ± 6.7** |
| 2i | $CH_2$ | $(CH_2)_{13}$ | $CH_2OH$ | 129.4 ± 5.0** | 160.8 ± 13.8** |

[a]SEM = Standard error at the mean obtained on three independent experiments for which conditions are replicated three times.
[b]$\Delta$ = [CH=CH—$CH_2$—CH=CH—$(CH_2)_4$—$CH_3$]
*P < 0.05 vs control, One-way ANOVA, Dunnett's post-hoc analysis or t-test
**P < 0.001 vs control, One-way ANOVA, Bonferroni's post-hoc analysis.

All compounds in this series have a capacity to induce a neuritogenesis at nanomolar concentrations. The neuroprotective potential of these compounds appears to be better for compounds with an amine rather than an amide function (see 1c vs 2c), the best activities being observed for compound 2c. Variations as a function of the length of the chain are minimum, however it is observed that the shortest compounds are slightly less active. Concerning the presence of unsaturations, no variation was observed for the two activities (see 2h vs 2e). The terminal hydroxyl function improves the two activities only in amine series.

These results show an important role of the intrachain amine that gives this series the required double activity. Nevertheless, the best neuroprotective potentials are observed for chain lengths after the nitrogen atom (in other words $X_1$—$X_2$—$R_2$) longer than or equal to 15 carbon atoms (namely chain length $X_2$ longer than or equal to 13 carbon atoms), possibly carrying a terminal hydroxyl. The best combined activities were obtained with compounds 2c and 2i.

2.2 Anti-oxidant Capacity of Compounds According to the Invention

Two tests were used to evaluate the anti-oxidant capacity of compounds according to the invention, i.e. their capability to neutralise free radicals.

Test with ABTS

ABTS or 2,2'-azino-bis-(3-ethylbenzthiazoline-6-sulfonic) acid is a coloured indicator of the presence of hydroxyl radicals in solution. The attack of a hydroxyl radical on ABTS generates the formation of an $ATBS^+$. cation radical (Equation 1). This coloured entity makes the absorbance (Abs) of the solution equal to 450 nm.

$$ABTS + HO. \dashrightarrow ABTS^+. + HO^- \qquad \text{Equation 1}$$

During the test, hydroxyl radicals are generated by Fenton's reaction in the presence of iron and hydrogen peroxide (Equation 2)

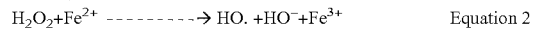

$$H_2O_2 + Fe^{2+} \dashrightarrow HO. + HO^- + Fe^{3+} \qquad \text{Equation 2}$$

When a radical trap or antioxidant is present in solution, competition with ABTS is set up for reduction of hydroxyl radicals, which reduces the absorbance (Abs) at 450 nm.

The percentage of hydroxyl radicals converted into hydroxyl ions (% conversion) by the compound of interest may be calculated using Formula 1:

$$\% \text{ conversion} = \frac{Abs_{ABTS} - Abs_{ABTS+product}}{Abs_{ABTS}} \times 100 \qquad \text{Formula 1}$$

The anti-oxidant capacity of a compound may then be expressed in the form of $IC_{50}$ that reflects the concentration at which 50% of hydroxyl radicals have been reduced by the tested compound.

Thus, the compounds to be tested and Trolox® were solubilised in ethanol so as to obtain solutions at 1 mM. We used cascade dilutions to obtain a concentration range varying from 1 mM to 10 nM. 90 µL of a 1:1 water-ethanol mixture was then added onto an ELISA 96-well plate, followed by 15 µL of an aqueous solution of ABTS at 1 mM, 15 µL of an aqueous solution of $Fe_2SO4$ at 0.5 mM, 15 µL of each compound to be tested at different concentrations, and then 15 µl of an aqueous solution of hydrogen peroxide at 100 mM. The mixtures thus obtained were stirred at ambient temperature sheltered from air for 30 minutes, and the value of the absorbance at 405 nm was then measured. The capacity of each compound to reduce hydroxyl radicals is determined by the reduction in absorbance at 450 nm, the control solution being composed of pure ethanol. Therefore, the ABTS test was made in comparison with Trolox®. The same ranges from 10 nm to 1 mM of indoles 1a, 1c, 1g, 1i, 2a, 4c, 2g, 2h and 2i were tested.

TABLE 2

| Compound | | IC$_{50}$ ± SEM$^a$ (mM) |
|---|---|---|
| Trolox ® | | 0.55 ± 0.02 |
| [tryptamine-NH-(CH$_2$)$_n$-CH$_3$ structure] | (n = 9) 2a<br>(n = 12) 2c<br>(n = 19) 2g | 0.81 ± 0.14<br>0.62 ± 0.05<br>0.67 ± 0.01 |
| [tryptamine-NH-(CH$_2$)$_6$-CH=CH-CH$_2$-CH=CH-(CH$_2$)$_4$-CH$_3$ structure] | 2h | 0.34 ± 0.01 |
| [tryptamine-NH-(CH$_2$)$_{11}$-OH structure] | 2i | 0.73 ± 0.01 |

$^a$SEM: Standard error at the mean obtained on three independent experiments.

Interestingly, IC$_{50}$ values of tested amine compounds 2a, 2c, 2g, 2h and 2i according to the invention are close to the one for Trolox®, demonstrating the interest of the amine function in the anti-oxidant activity of these compounds. The presence of double intrachain bonds improves the anti-oxidant activity leading to a lower IC$_{50}$ value than Trolox® (see 2h).

Cellular Test with Dihydrorhodamine 123

Dihydrorhodamine 123 or DHR123 is used as an indicator of reactive oxygen species (ROS). It is uncharged and not fluorescent and passes passively through the cellular membrane before being oxidised in contact with free radicals, into rhodamine 123 emitting green fluorescence.

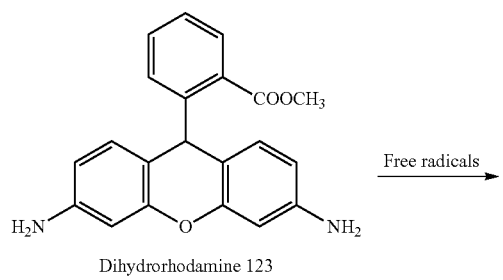
Dihydrorhodamine 123
→ Free radicals

-continued

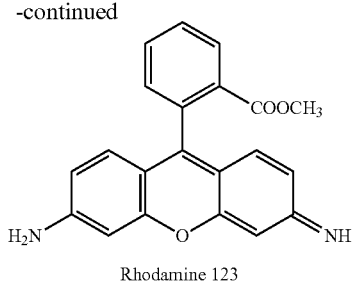
Rhodamine 123

The quantity of intracellular ROS is reduced when the cells are treated by an anti-oxidant. This reduction results in a quantifiable decay in emitted fluorescence in the presence of DHR123.

In order to conclude the role of the anti-oxidant capacity of compounds according to the invention in the observed neuroprotectrive activity, the cultures were placed strictly under the same conditions as for the neuroprotection/neuritogenesis test. Thus, the cultures were kept for eight days in the presence of a concentration of 10 nM of each of the tested tryptaminic derivatives. On the 8$^{th}$ day in vitro (DIV 8), 50 μM of DHR-123 (Sigma) was added and the cells were incubated for 30 minutes at 37° C. They were then washed three times, treated once again by compounds according to the invention and placed in a medium without any phenol red. Living fluorescent neurones that were immediately photographed can be observed, the fluorescence density per neurone being quantified under an inverted fluorescence microscope by an image analysis software. The results obtained are given in Table 3 below.

TABLE 3

| Compound | | IF/neurone (%) |
|---|---|---|
| Control | | 100.0 ± 3.3 |
| Trolox ® | | 44.0 ± 2.8** |
| 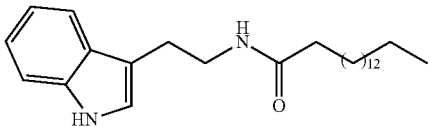 | 1c | 55.9 ± 3.0** |
| 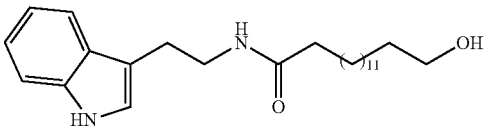 | 1i | 56.5 ± 2.7** |
| 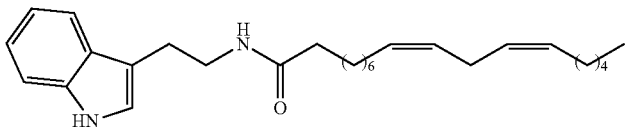 | 1h | 60.9 ± 6.4** |
| 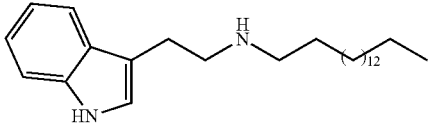 | 2c | 47.8 ± 4.7** |
| 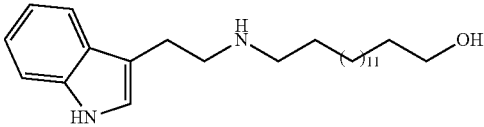 | 2i | 44.0 ± 3.6** |
| 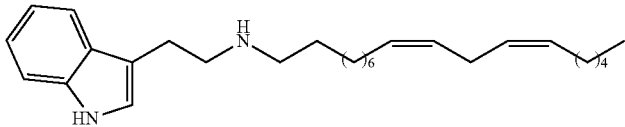 | 2h | 43.7 ± 5.2** |
| 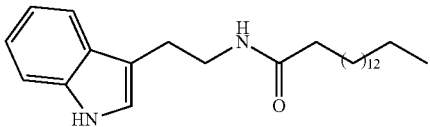 | 1c | 55.9 ± 3.0 ** |

[a]Standard error at the mean obtained on three independent experiments.
**P <0.001 vs control, One-way ANOVA, Bonferronni's post-hoc analysis.

Figure 1:
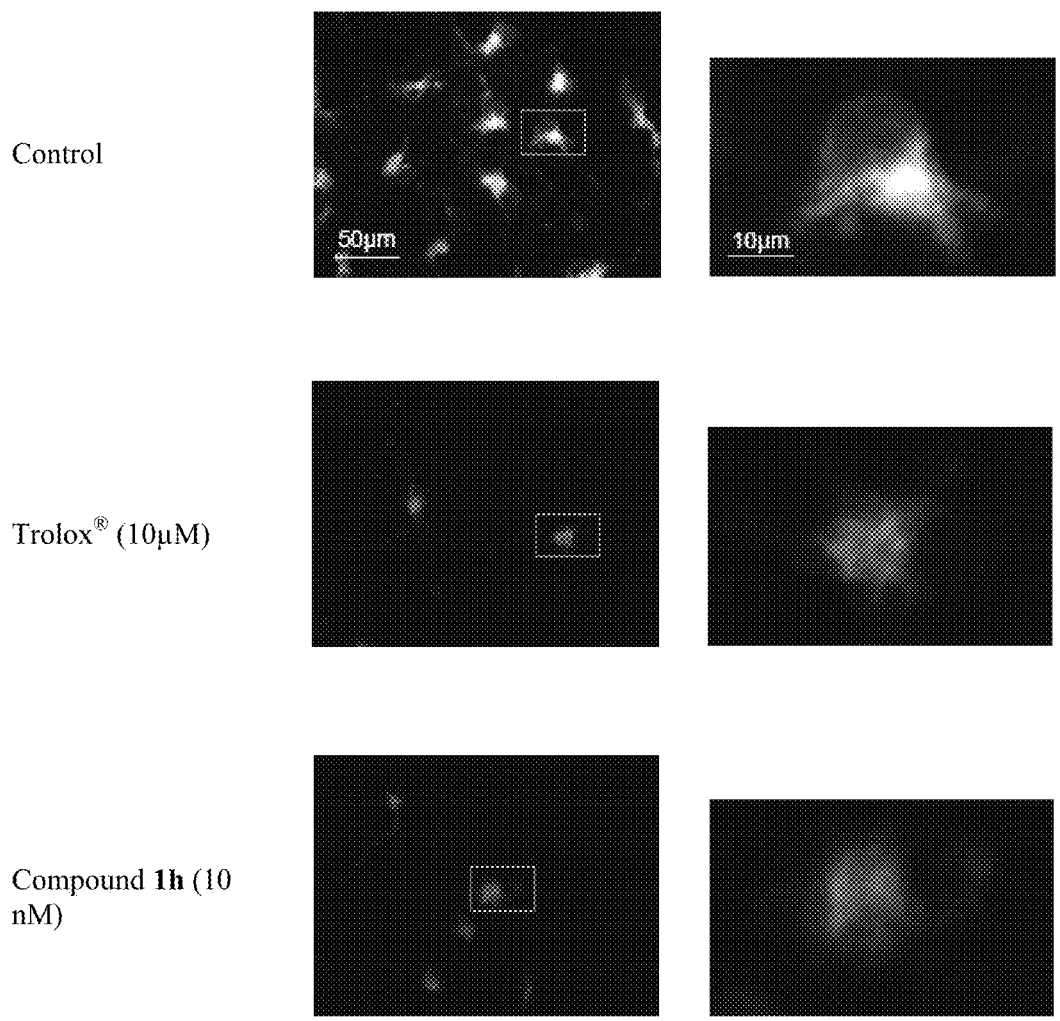
FIG. 1 shows photographs of fluorescent neurons obtained under DHR-123 test conditions without treatment (control) or after treatment with Trolox® at 10 µM or with compound 1 h at 10 nM.

Neurones of cultures treated by tryptaminic derivatives at 10 nM have a significantly lower cytoplasmic quantity of ROS than the untreated cultures, which results in a reduction of 40-60% of the emitted fluorescence. Therefore, these compounds have a large anti-oxidant activity of the order of the value observed for the reference compound, and always with a better activity of amine derivatives compared with amide derivatives (see 1i vs 2i, and 1h vs 2h). FIG. 1 also illustrates the reduction of the fluorescence intensity emitted in the neurones after treatment by compound 1h at 10 nM, this compound having the best anti-oxidant activity in comparison with Trolox® and the untreated control.

The strong anti-oxidant capacity observed for tryptaminic derivatives under conditions and at concentrations necessary to observe their neuroprotective activity, could be one element towards an answer about the action mechanisms of these compounds in the neuroprotective component.

Therefore, these compounds are very interesting because they combine both a protective and regenerative effect, applicable in the treatment of neurodegenerative diseases.

2.3 Study of the Passage Through the Blood-brain Barrier (BBB)

This study was done using compound 2c as the compound according to the invention.

The purpose of this study is to use HPLC coupled with a mass spectrometer to verify the presence of molecule 2c according to the invention in the cerebral hydrochloride of molecule 2c (2c/HCl) by oral or intra-peritoneal (IP)pathway.

Equipment and Methods

Animals: Male RjOrl: SWISS mice approximately 5 weeks old and weighing between 20 and 24 g on arrival (from the R Janvier Breeding Centre, France) are kept in the animal house at constant temperature (22±1° C.) and under controlled hygrometry (55±20%) with a 12 hours light/darkness cycle (8 h00-20 h00). The mice were allowed free access to food and drink during the acclimatisation and study period. All experiments took place in accordance with the conditions defined in decree No. 2001-464, May 29, 2001 dealing with experiments on animals.

Treatments: Two 5-day sub-chronic treatments were done (oral or intra-peritoneal pathway):

Treatment by Intra-Peritoneal Pathway (IP):

The solution of hydrochloride of 2c/HCl to be injected is prepared in the carrier (10% Tween20+20% DMSO+70% NaCl at 09% in water) at a concentration of 2.0 g/L. Three groups were formed:

(1) mice that received the carrier through the IP pathway, at 10 mL/kg (group N, n=4),
(2) mice treated with 2c/HCl by IP pathway, at 20 mg/kg and at 10 mL/kg (group R, n=6), and
(3) Control mice that received no treatment (n=2).

The treated mice R4, R5 and R6 and the carrier mice N1, N2, N3 and N4 received the following treatments:

| Monday 7 Dec. 2009 | Tuesday 8 Dec. 2009 | Wednesday 9 Dec. 2009 | Thursday 10 Dec. 2009 | | Friday 11 Dec. 2009 | |
| --- | --- | --- | --- | --- | --- | --- |
| 15 h 20 | 12 h 10 | 13 h 45 | 12 h 45 | 17 h 30 | 11 h 20 | Euthanasia between 15 h 20 and 17 h 40 |

Treated mice R1, R2 and R3 received the same treatments as the previous mice except on Thursday, when they did not receive the second treatment.

| Monday 7 Dec. 2009 | Tuesday 8 Dec. 2009 | Wednesday 9 Dec. 2009 | Thursday 10 Dec .2009 | Friday 11 Dec. 2009 | |
| --- | --- | --- | --- | --- | --- |
| 15 h 20 | 12 h 10 | 13 h 45 | 12 h 45 | 11 h 20 | Euthanasia between 13 h 25 and 14 h 55 |

Treatment by Oral Pathway (per os):

The solution of hydrochloride of 2c to be administered is prepared in the carrier (0.5% Tween80+99.5% carboxy-methyl cellulose at 1%, in 0.9% NaCl in water) at a concentration of 15.0 g/L.

Three groups were formed:
(1) mice that received the carrier at 10 mL/kg by oral pathway (Group V, n=4),
(2) mice treated with 2c/HCl by oral pathway at 150 mg/kg and at 10 mL/kg (Group B, n=6), and
3) control mice that did not receive any treatment (n=2).

All mice were treated twice per day for 4 days. On the $5^{th}$ day, they received a final treatment and were euthanized between 3 h00 and 7 h30 after this last treatment, according to the following scheme:

Euthanasia: The mice are anaesthetised by the injection of 0.1 mL of a solution of sodium pentobarbital at 6% and an perfusion is then done on the mice so as to remove all traces of blood from the brain, with an 0.9% NaCl solution that contains heparin (200 μL of heparin choay at 5000 UI/mL in 1 liter of 0.9% NaCl). An perfusion with a minimum of 50 mL of this solution is done on each animal. The mouse brain is removed. The cerebellum, the brain stem and olfactory bulbs are eliminated.

Figure 2:
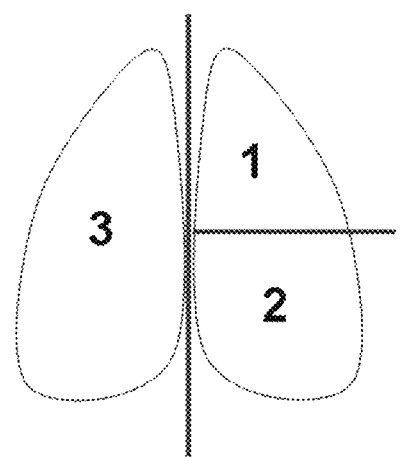
FIG. 2 shows the section of the brain in 3 parts made in example 2.3.

The brain is dissected into 3 parts according to the scheme presented in FIG. 2. The 3 parts of the brain are frozen in isopentane at −30° C. for one minute, and then kept separately at −80° C.

Extraction method: Each brain sample is weighed, homogenised in MeOH (100 μL of MeOH for 10 mg of brain tissue) and is then mixed by sonication. The suspensions thus obtained are centrifuged at 27 000 g at 4° C. for 10 minutes. The floats, diluted to half in MeOH, are transferred in HPLC vials for analysis of compound 2c by HPLC-MS/MS.

However, only parts 1 of the mice brains were extracted and analysed so as to keep samples for future analyses. Nevertheless, the three parts of the brain of a mouse in each group (IP and per os) were extracted in order to verify that compound 2c is not distributed preferentially into one of these 3 parts.

All samples were stored at −4° C. before and during the analyses. All analyses of all samples were done on the same day, under the same conditions.

Positive and negative controls: Brains of carrier mice were used for positive and negative controls. For the positive control, 10 μl of a solution of hydrochloride of 2c at 1 μg/mL is added to the float and diluted to half into MeOH before transfer in an HPLC vial.

| Monday 7 Dec. 2009 | | Tuesday 8 Dec. 2009 | | Wednesday 9 Dec. 2009 | | Thursday 10 Dec. 2009 | | Friday 11 Dec. 2009 | |
| --- | --- | --- | --- | --- | --- | --- | --- | --- | --- |
| 13 h 00 | 17 h 20 | 10 h 50 | 16 h 10 | 10 h 50 | 17 h 05 | 10 h 40 | 17 h 10 | 10 h 30 | Euthanized between 13 h 30 and 18 h 00 |

Preparation of the range of compound 2c: A primary solution of hydrochloride of 2c is prepared extemporaneously in MeOH at a concentration of 1.0 mg/mL. All other solutions are prepared by dilution of this primary solution in MeOH and then stored at −4° C.

Instrumentation and conditions for analysis of compound 2c: Detection and quantification based on the area of the peaks are done using HPLC-MS/MS, in MRM mode.

The HPLC system is composed of a Dionex Ultimate 3000 pump equipped with a Dionex WPS-3000PL autosampler. The mass spectrometer used is a Water-Micromass Quattro Ultima spectrometer equipped with an electrospray ionisation source and a triple quadrupole analyser. Data and analyses are acquired using Masslynx 3.5.

Liquid chromatography is done in isocratic mode using an XBridge™ C 18, 150×2.1 mm column (Waters), with a particle size of 3.5 µm. The mobile phase is composed of a mixture of two phases A and B in the proportion 3:97. Phase A is composed of 0.2% (v/v) triethylamine in water (pH=11.5). Phase B is composed of 0.2% triethylamine in MeOH (v/v). The flow is fixed at 0.2 mL/min and the injection volume is 10 µL.

The mass spectrometer is connected to the HPLC system using an electrospray ionisation source. A switching valve is programmed to discard the first three minutes of chromatography in order to prevent the accumulation of salt at the source capillary. The capillary voltage is adjusted to 3000 V and the cone voltage to 50 V, the source temperature is adjusted to 120° C., the precipitation gas ($N_2$) is adjusted to a flow of 463 L/h and the temperature to 350° C. Mass spectra are obtained in positive mode. Parameters are optimised to obtain the maximum of molecular ions at m/z 385.66, corresponding to compound 2c. Collision is obtained using an inert gas (argon) and energy is fixed at 22 eV in MS/MS mode to detect mass transitions: m/z 385.66→254.23 and 385.66→144.17.

The calibration straight line is made using a standard procedure comprising 7 concentrations (0.5 µg/mL; 0.1 µg/mL; 20 ng/mL; 4 ng/mL; 0.8 ng/mL; 0.16 ng/mL and 0.08 ng/mL).

Results

Validation of the HPLC-MS/MS method: The area of HPLC peaks depends on the concentration of compound 2c within the range from 0.16 to 500.00 ng/mL with $R^2$ equal to 0.9997. The detection limit is 0.08 ng/mL with an S/N (signal/noise) ratio equal to 3:1. The retention time of compound 2c is 5.3 minutes and the acquisition time is 8 minutes.

Concentration of Compound 2c in Brain Extracts:

Per os Pathway:

The chromatograms obtained are shown in FIG. 3. Compound 2c cannot be detected in the brain extract from mice treated by the carrier and is quantified at 20.31 ng/mL in the positive control. Compound 2c is quantified in brain extracts from mice treated per os at an average concentration of 21.25 ng/mL±0.82 SEM (n=8).

IP Pathway:

The chromatograms obtained are shown in FIG. 4. Compound 2c is not detectable in the brain extract from mice treated by the carrier and is quantified at 19.48 ng/mL in the positive control. Compound 2c is quantified in brain extracts from mice IP treated at an average concentration of 14.73 ng/mL±0.58 SEM (n=8).

Discussion and Conclusion

Compound 2c is capable of crossing the BBB in vivo after IP administration and after per os administration of 2c/HCl. The treatment with the per os pathway at 300 mg/kg/d allows giving concentrations about 1.5 times higher than those obtained after an IP treatment at 20 mg/kg/d.

Abbreviations Used:

| | |
|---|---|
| EDC | 1-(3-Dimethylaminopropyl)-3-ethylcarbodiimide hydrochloride |
| ESI-MS | Mass spectroscopy in electrospray mode |
| GC | Gaseous phase chromatography |
| HOBt | N-Hydroxy benzotriazole |
| HPLC | High Performance Liquid Chromatography |
| HPLC-MS/MS | High Performance Liquid Chromatography coupled with a tandem mass spectrometer |
| IR | Infrared absorption |
| MRM | Multiple Reaction Monitoring |
| NMR$^1$H | Nuclear Magnetic resonance of the proton |
| NMR$^{13}$C | Nuclear magnetic resonance of carbon |

The invention claimed is:

1. A method for treating Parkinson's disease, multiple sclerosis or a cerebrovascular accident comprising the administration to a person in need thereof of an effective quantity of a compound of the following formula (I):

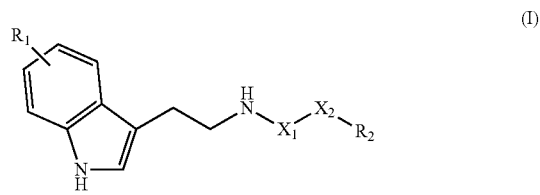

or a pharmaceutically acceptable salt thereof, a stereoisomer or a mixture of stereoisomers in any proportion, in which:

$X_1$ represents a $CH_2$ or $C=O$ group;

$X_2$ represents a saturated or unsaturated linear hydrocarbon chain having 8 to 24 carbon atoms;

$R_1$ represents a hydrogen atom or an OH or ($C_1$-$C_6$) alcoxy group; and $R_2$ represents a $CH_3$ or $CH_2OR_3$ group, where $R_3$ represents an atom of hydrogen or a ($C_1$-$C_6$)alkyl, CO—($C_1$-$C_6$)alkyl or NH—($C_1$-$C_6$)alkyl group.

2. The method according to claim 1, wherein the compound of formula (I) satisfies the following formula (Ia):

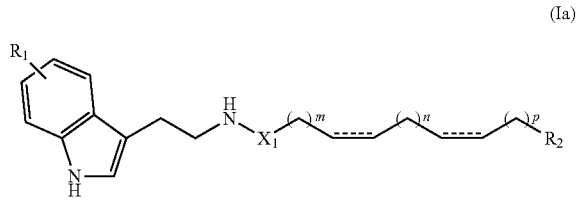

in which:

- - - - independently represents a single or double bond;

m represents an integer greater than or equal to 1, and n and p represent, independently of each other, an integer greater than or equal to 0 where 8 ≤m +n +p +4 ≤24.

3. The method according to claim 1, wherein the compound of formula (I) satisfies the following formula (Ib) or (Ic):

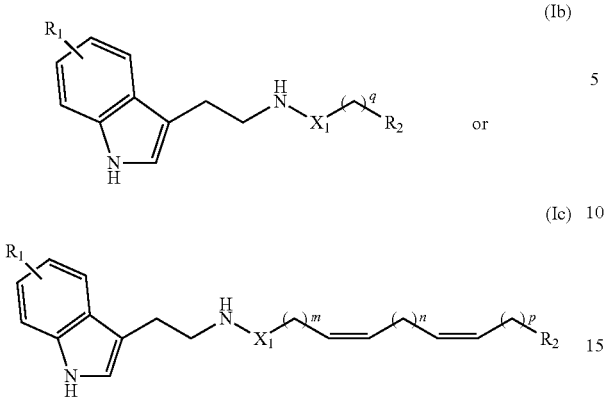
in which:
q represents an integer between 8 and 24, and
m represents an integer greater than or equal to 1, and n and p represent, independently of each other, an integer greater than or equal to 0 where 8 ≤m +n +p +4 ≤24.
4. The method according to claim 1, wherein the compound of formula (I) is chosen from among:
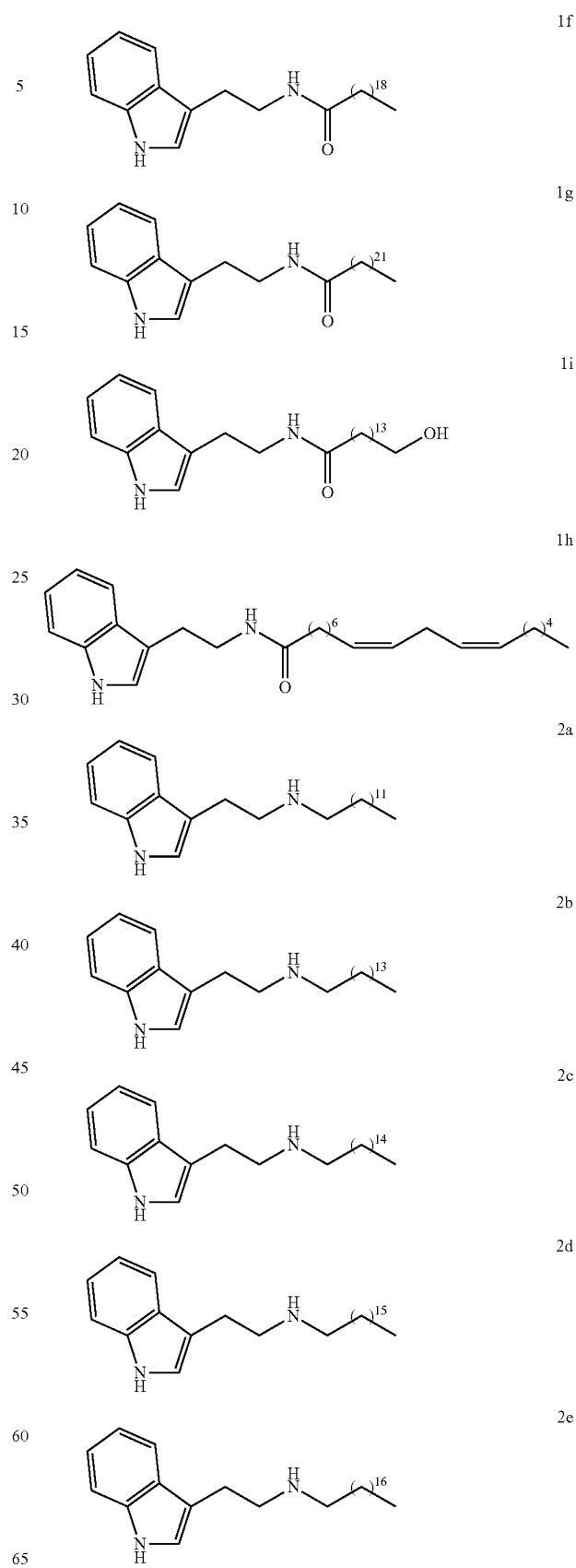

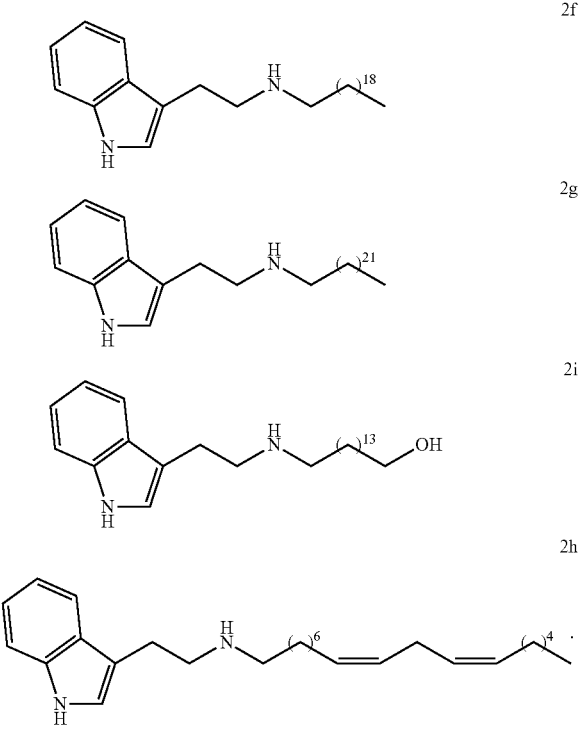

5. A compound of the following formula (I):

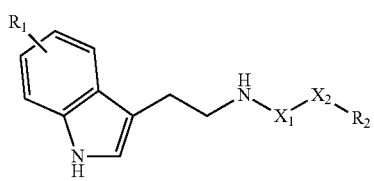

or a pharmaceutically acceptable salt thereof, a stereoisomer or a mixture of stereoisomers in any proportion, in which:
- $X_1$ represents a $CH_2$ group;
- $X_2$ represents a saturated or unsaturated linear hydrocarbon chain having 8 to 24 carbon atoms;
- $R_1$ represents a hydrogen atom or an OH or ($C_1$-$C_6$) alcoxy group; and
- $R_2$ represents a $CH_3$ or $CH_2OR_3$ group, where $R_3$ represents an atom of hydrogen or a ($C_1$-$C_6$)alkyl, CO—($C_1$-$C_6$)alkyl or NH—($C_1$-$C_6$)alkyl group.

6. The compound according to claim 5, satisfying the following formula (Ia):

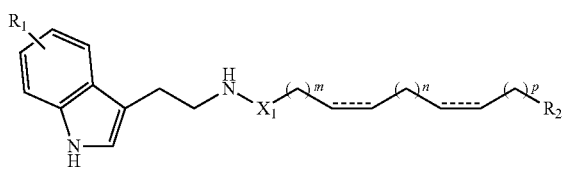

in which:
- ---- independently represents a single or double bond, and
- m represents an integer greater than or equal to 1, and n and p represent, independently of each other, an integer greater than or equal to 0, where $8 \leq m + n + p + 4 \leq 24$.

7. The compound according to claim 5, satisfying the following formula (Ib) or (Ic):

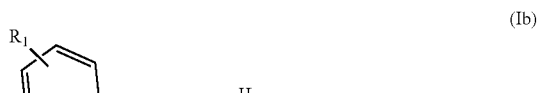

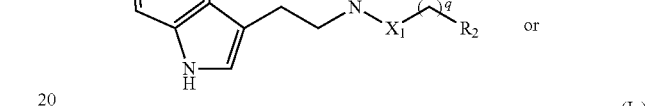

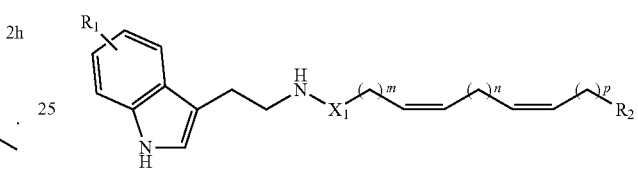

in which:
- q represents an integer between 8 and 24, and
- m represents an integer greater than or equal to 1, and n and p represent, independently of each other, an integer greater than or equal to 0, where $8 \leq m + n + p + 4 \leq 24$.

8. The compound according to claim 5, chosen from among:

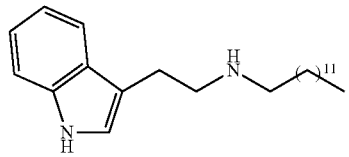

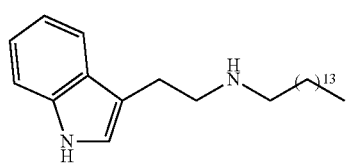

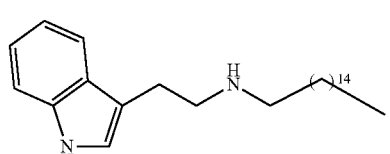

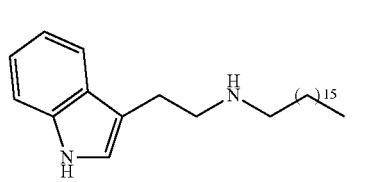

-continued

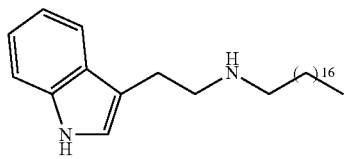

2e

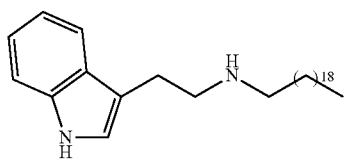

2f

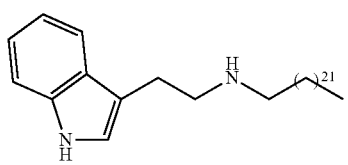

2g

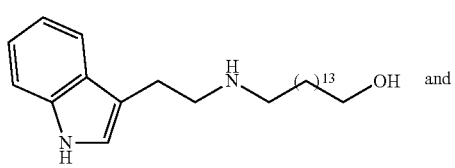

2i

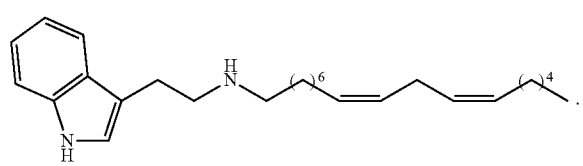

2h

9. A pharmaceutical composition comprising at least one compound according to claim 5 and a pharmaceutically acceptable carrier.

10. The pharmaceutical composition according to claim 9, comprising another active principle.

11. The pharmaceutical composition according to claim 10, wherein the other active principle is chosen from among acetylcholinesterase inhibitors; monoamine oxydase inhibitors; O-methyltransferase catecholamine inhibitors; glutamatergic inhibitors; cholinergic agonists; dopaminergic agonists; neuromediator analogues or precursors e; and anticholinergics.

12. The pharmaceutical composition according to claim 11, wherein the acetylcholinesterase inhibitor is chosen from donezepil, galanthamine, rivastigmine, memantine and tacrine; the monoamine oxydase inhibitor is selegiline; the O-methyltransferase catecholamine inhibitor is entacapone; the glutamatergic inhibitor is chosen from amantadine and baclofen; the cholinergic agonist is sabcomeline; the dopaminergic agonist is chosen from pergolide, cabergoline, ropirinole and pramipexole; the neuromediator analogue or precursor is L-3,4-dihydroxyphenylalanine; and the anticholinergic is chosen from trihexyphenidyl and tropatepine.

13. A method for treating Alzheimer's disease, Parkinson's disease, multiple sclerosis or a cerebrovascular accident comprising the administration to a person in need thereof of an effective quantity of a pharmaceutical composition according to claim 9.

14. A method for the preparation of a compound of formula (I) according to claim 1, comprising the following steps:
(a) coupling between tryptamine and a compound of the following formula (II):

$$Z-X_2-R_2 \quad (II)$$

for which Z represents a free form or an active form of a carboxylic acid function and $R_2$ and $X_2$ are as defined in claim 1,
to give a compound of the following formula (I-1):

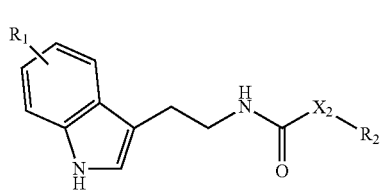

(I-1)

in which $R_1$, $R_2$ and $X_2$ are as defined in claim 1,
(b) optionally reduction of the carbonyl function of the compound of formula (I-1) obtained in step (a) above to give a compound of the following formula (I-2):

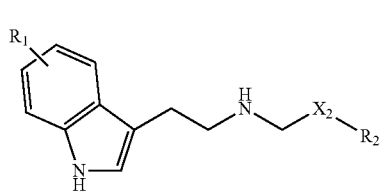

(I-2)

for which $R_1$, $R_2$ and $X_2$ are as defined in claim 16, and
(c) separation of the compound (I-1) or (I-2) obtained in the previous step, from the reaction medium.

15. The method according to claim 14, wherein step (a) is performed with a compound of structure (II) in which $Z=CO_2H$ in the presence of a coupling agent chosen from diisopropylcarbodiimide, dicyclohexylcarbodiimide, 1-(3-dimethylaminopropyl)-3-ethylcarbodiimide hydrochloride, carbonyldiimidazole, 2-H-benzotriazole-1-yl)-1,1,3,3-tetramethyluronium hexafluorophosphate, 2-(1H-benzotriazole-1-yl)-1,1,3,3-tetramethyluronium tetrafluoroborate or O-(7-azabenzotriazol-1-yl)-1,1,3,3-tetramethyluronium hexafluorophosphate, possibly associated with a coupling auxiliary chosen from N-hydroxy succinimide, N-hydroxy benzotriazole, 3,4-dihydro-3-hydroxy-4-oxo-1,2,3-benzotriazole, 1-hydroxy-7-azabenzotriazole or N-hydroxysulfosuccinimide.

16. The method according to claim 14, wherein step (a) is performed with a compound of structure (II) in which $Z=COCl$ possibly in the presence of a base.

17. The method according to claim 16, wherein the base is triethylamine.

18. The method according to claim 14, wherein step (b) is performed in the presence of a hydride.

19. The method according to claim 18, wherein the hydride is $LiAlH_4$.

20. The compound according to claim 1, wherein $R_1$ represents a hydrogen atom.

21. The compound according to claim 1, wherein $R_2$ represents a $CH_3$ or $CH_2OH$ group.

22. The compound according to claim 1, wherein $X_1$ represents a $CH_2$ group.

23. The compound according to claim 5, wherein $R_1$ represents a hydrogen atom.

24. The compound according to claim 5, wherein $R_2$ represents a $CH_3$ or $CH_2OH$ group.

* * * * *